United States Patent
Ferretti et al.

(10) Patent No.: US 11,419,870 B2
(45) Date of Patent: Aug. 23, 2022

(54) INTERMITTENT DOSING OF MDM2 INHIBITOR

(71) Applicant: Novartis AG, Basel (CH)

(72) Inventors: Stephane Ferretti, Huningue (FR); Sebastien Jeay, Niffer (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/898,886

(22) Filed: Jun. 11, 2020

(65) Prior Publication Data

US 2021/0000824 A1 Jan. 7, 2021
US 2022/0233530 A9 Jul. 28, 2022

Related U.S. Application Data

(63) Continuation of application No. 16/221,650, filed on Dec. 17, 2018, now abandoned, which is a continuation of application No. 15/849,770, filed on Dec. 21, 2017, now abandoned, which is a continuation of application No. 15/321,042, filed as application No. PCT/IB2015/054792 on Jun. 25, 2015, now abandoned.

(60) Provisional application No. 62/017,406, filed on Jun. 26, 2014.

(51) Int. Cl.
| | | |
|---|---|---|
| A61K 31/506 | (2006.01) | |
| A61K 31/402 | (2006.01) | |
| A61K 31/404 | (2006.01) | |
| A61K 31/4178 | (2006.01) | |
| A61K 31/4418 | (2006.01) | |
| A61K 31/4439 | (2006.01) | |
| A61K 31/47 | (2006.01) | |
| A61K 31/472 | (2006.01) | |
| A61K 31/496 | (2006.01) | |
| A61K 9/00 | (2006.01) | |
| A61K 45/06 | (2006.01) | |

(52) U.S. Cl.
CPC .......... *A61K 31/506* (2013.01); *A61K 9/0019* (2013.01); *A61K 31/402* (2013.01); *A61K 31/404* (2013.01); *A61K 31/4178* (2013.01); *A61K 31/4418* (2013.01); *A61K 31/4439* (2013.01); *A61K 31/47* (2013.01); *A61K 31/472* (2013.01); *A61K 31/496* (2013.01); *A61K 45/06* (2013.01)

(58) Field of Classification Search
CPC .................................................. A61K 31/506
USPC ........................................................ 514/274
See application file for complete search history.

(56) References Cited

U.S. PATENT DOCUMENTS

| | | | |
|---|---|---|---|
| 8,815,926 B2 | 8/2014 | Furet et al. | |
| 9,051,279 B2 | 6/2015 | Berghausen et al. | |
| 9,371,568 B2 | 6/2016 | Gaulis et al. | |
| 9,403,827 B2 | 8/2016 | Furet et al. | |
| 9,556,180 B2 | 1/2017 | Furet et al. | |
| 10,220,038 B2 | 3/2019 | Ferretti et al. | |
| 10,935,540 B2 | 3/2021 | Guerreiro et al. | |
| 10,966,978 B2 | 4/2021 | Ferretti et al. | |
| 2011/0230457 A1 | 9/2011 | Berghausen et al. | |
| 2013/0245039 A1 | 9/2013 | Higgins et al. | |
| 2013/0245089 A1 | 9/2013 | Glenn et al. | |
| 2014/0011798 A1 | 1/2014 | Furet et al. | |
| 2014/0140898 A1 | 5/2014 | Hakansson | |
| 2014/0148494 A1 | 5/2014 | Wang et al. | |
| 2014/0323482 A1 | 10/2014 | Ma et al. | |
| 2015/0218274 A1 | 8/2015 | Sabatos-peyton et al. | |
| 2017/0196866 A1 | 7/2017 | Ferretti et al. | |
| 2017/0196886 A1 | 7/2017 | Ferretti et al. | |
| 2018/0110779 A1 | 4/2018 | Ferretti et al. | |
| 2019/0060309 A1 | 2/2019 | Halilovic et al. | |
| 2019/0209561 A1 | 7/2019 | Ferretti et al. | |
| 2020/0281910 A1 | 9/2020 | Caponigro et al. | |
| 2020/0281925 A1 | 9/2020 | Ferretti et al. | |
| 2021/0000824 A1 | 1/2021 | Ferretti et al. | |
| 2021/0087194 A1 | 3/2021 | Wang et al. | |

FOREIGN PATENT DOCUMENTS

| | | | |
|---|---|---|---|
| WO | 02/064214 A2 | 8/2002 | |
| WO | 03/043632 A2 | 5/2003 | |
| WO | 2006/091646 A2 | 8/2006 | |
| WO | 2011076786 A1 | 6/2011 | |
| WO | 2012080389 A1 | 6/2012 | |
| WO | 2013111105 A1 | 8/2013 | |
| WO | 2014020502 A2 | 2/2014 | |
| WO | 2015082384 A1 | 6/2015 | |

(Continued)

OTHER PUBLICATIONS

Hyman, D. et al.: "Dose- and regimen-finding phase I study of NVP-HDM201 in patients (pts) with TP53 wild-type (wt) advanced tumors", European Journal of Cancer, vol. 69, Dec. 1, 2016, abstract.

Hyman, D. M. et al.: Dose- and Regimen-finding Phase I Study of NVP-HDM201 in Patients With TP53 Wild-type Advanced Tumors, Dec. 2, 2016, Retrieved from the Internet: URL:http://www.poster-submission.com/ena2016/visitors/eposter/33139, the whole document.

(Continued)

*Primary Examiner* — Taofiq A Solola
(74) *Attorney, Agent, or Firm* — Elizabeth T. Karnas

(57) ABSTRACT

The present disclosure relates to mdm2 inhibitors for use in specific dosing schedules. It was found that if sufficiently potent or, in alternative, sufficiently high dose of a Mdm2 inhibitor is used, it can cause antineoplastic effect by triggering much longer lasting antiproliferative mechanism in cells. The long lasting effect can sustain for several weeks after a single dose, which eliminates the need for daily treatment and allows administering the Mdm2i intermittently. A treatment with the intermittent dosing schedule of a Mdm2 inhibitor can be combined with a daily treatment of the Mdm2i or with another pharmaceutically acceptable ingredient.

4 Claims, 26 Drawing Sheets

(56) References Cited

FOREIGN PATENT DOCUMENTS

| WO | 2015198266 | A1 | 12/2015 |
|---|---|---|---|
| WO | 2016/127135 | A1 | 8/2016 |
| WO | 2016167236 | A1 | 10/2016 |
| WO | 2017037579 | A1 | 3/2017 |
| WO | 2018092020 | A1 | 5/2018 |
| WO | 2018158225 | A1 | 9/2018 |
| WO | 2018178925 | A1 | 10/2018 |
| WO | 2019180576 | A1 | 9/2019 |
| WO | 2020092221 | A1 | 5/2020 |
| WO | 2020128892 | A1 | 6/2020 |
| WO | 2020128894 | A1 | 6/2020 |
| WO | 2020128898 | A1 | 6/2020 |
| WO | 2020202052 | A1 | 10/2020 |

OTHER PUBLICATIONS

Higgins, B. et al: "Preclinical Optimization of MDM2 Antagonist Scheduling for Cancer Treatment by Using a Model-Based Approach", Clinical Cancer Research, vol. 20, No. 14, Jul. 15, 2014, pp. 3742-3752.
Davidson-Moncada, J. et al.: "Dissecting the Immune Landscape of Acute Myeloid Leukemia", Biomedicines, vol. 6, No. 4, Nov. 25, 2018, p. 110.
Anonymous: "History of Changes for Study: NCT03940352 HDM201 in Combination With MBG453 or Venetoclax in Patients With Acute Myeloid Leukemia (AML) or High-risk M Syndrome (MDS)", Clinicaltrials.gov archive, Oct. 15, 2019, pp. 1-5.
Iancu-Robin et al.: "Activation of p53 by MDM2 inhibitor RG7112 impair thrombopoiesis", Experimental Hermatology, (2014), vol. 42, pp. 137-145.
Handbook Anti-Tumor Chemotherapy, Ed. Translator NI M., Medicine 1993 p. 124, section Chemodectomy, p. 147 2nd paragraph—1926-28.
Anti-Tumor Chemotherapy Handbook, 2nd Edition, Ed. Translator NI M., Medicine 1993, p. 124, Section Chermodectomy, p. 147, 2nd paragraph, pp. 14926-28 (English Translation Only).
Hollenbach, et al. "A Comparison of Azacitidine and Decitabine Activities in Acute Myeloid Leukemia Cell Lines", PLoS One, 5(2):e9001, Feb. 2010.
International Preliminary Report on Patentability, dated Sep. 14, 2016 in international Application No. PCT/IB2015/054792, 7 pages.
Kojima et al., "Pharmacological activation of wild-type p53 in the therapy of leukemia", International Society of Experimental Hematology, Jun. 18, 2016, pp. 791-798.
Hyman et al., "Dose and Regimen-finding Phase 1 Study of NVP-HDM201 in Patients with TP53 Wild-type Advanced Tumors", Novartis.
Anonymous, "History of Changes for Study: NCT02143635", U.S. National Library of Medicine, Clinical Trials.gov, Jun. 21, 2018, pp. 1-8.
Anonymous: "Early-Phase Trials of HDM201 Show Promise in Leukemias" May 1, 2017 https://www.ashclinicalnews.org/meeting-news/early-phase-trials-hdm2o1-show-promise-leukemias/, retrieved Jun. 21, 2018 pp. 1-4.
Jeay, Sebastien, et al., "Dose and Schedule Determine Distinct Molecular Mechanisms Underlying the Efficacy of the p53-MDM2 Inhibitor HDM201," Cancer Research, Nov. 1, 2018, pp. 6257-6267, vol. 78, American Association for Cancer Research.
Kurokawa, Tomohiro et al., "The Eltrombopag antitumor effect onhepatocelluar carcinoma," International Journal of Oncology, Nov. 1, 2015, pp. 1696-1702, vol. 47, No. 5.
Shangary, Sanjeev, et al., "Targeting the MDM2-p53 Interaction for Cancer Therapy," Clinical Cancer Research, Sep. 1, 2008, pp. 5318-5324, vol. 14, American Association for Cancer Research.
Supplementary data to Jeay, et al. "Dose and Schedule Determine Distinct Molecular Mechanisms Underlying the Efficacy of the p53-MDM2 Inhibitor HDM201," Cancer Research, Nov. 1, 2018, pp. 6257-6267, vol. 78, American Association for Cancer Research.
Hoe et al., "Drugging the p53 pathway: understanding the route to clinical efficacy," Nat Rev Drug Discov. 13(3):217-36 (2014).
Jeay et al., "A distinct p53 target gene set predicts for response to the selective p53-HDM2 inhibitor NVP-CGM097," Elife. 4:e06498 (23 pages) (2015).
Carry et al., "Inhibitors of the p53/hdm2 protein-protein interaction-path to the clinic," Bioorg Med Chem Lett. 23 (9):2480-5 (2013).
Goldstein et al., "Understanding wild-type and mutant p53 activities in human cancer: new landmarks on the way to targeted therapies," Cancer Gene Ther. 18(1):2-11 (2011).
Kitzen et al., "Phase I dose-escalation study of F60008, a novel apoptosis inducer, in patients with advanced solid tumours," Eur J Cancer. 45(10):1764-72 (2009).
Berry et al., "Continuous versus intermittent chemotherapy strategies in metastatic colorectal cancer: a systematic review and meta-analysis," Ann Oncol. 26(3):477-85 (2015).
Langenberg et al., "A phase 1 study of the MDM2 inhibitor AMG232 in patients with advanced p53 wild type (p53WT) solid tumors or multiple myeloma," Abstract of the poster presented at EORTC-NCI-ACCR on Nov. 29, 2016. Poster Sessions: Molecular Targeted Agents I: Poster (Board P053), Abstract 82, Eur J Cancer. 69(Suppl 1):S34, Dec. 1, 2016 (1 page).
Feretti et al., "Abstract 1224: Insights into the mechanism of action of NPHDM 201, a differentiated and versatile Next-Generation small-molecule inhibitor of MdM2, under evaluaton in phaseI clinical trials," Proceedings: AACR 107th Annual Meeting 2016; Apr. 16-20, New Orleans, published Jul. 2016 (4 pages).
Holzer et al., "Abstract 4855, Discovery of NVP-HDM201-First disclosure of a Next-Generation Mdm2 inhibitor with superior characteristics," Proceedings: AACR 107th Annual Meeting 2016; Apr. 16-20, New Orleans, published Jul. 2016 (4 pages).
Schöttle et al., "Intermittent high-dose treatment with erlotinib enhances therapeutic efficacy in EGFR-mutant lung cancer," Oncotarget. 6(36):38458-68 (2015).
Hyman et al., "Dose- and regimen-finding phase 1 study of NVP-HDM201 in patients (pts) with TP53 wild-type (wt) advanced tumors," Eur J Cancer, Supplement 1. S128:Board P070 (2016) (1 page).
Qin, J.-J. et al., "Natural Product MDM2 Inhibitors: Anticancer Activity and Mechanisms of Action," Current Medicinal Chemistry, (Nov. 1, 2012) v.19(33), pp. 5705-5725.
Tortora, Giampaolo, et al., "A novel MDM2 anti-sense oligonucleotide has anti-tumor activity and potentiates cytotoxic drugs acting by different mechanisms in human colon cancer," Int. J. Cancer, (Jul. 11, 2000), v.88(5), pp. 804-809.

INTERMITTENT DOSING OF MDM2 INHIBITOR

RELATED APPLICATIONS

The present disclosure is a continuation of U.S. patent application Ser. No. 16/221,650 filed Dec. 17, 2018, which is a continuation of U.S. patent application Ser. No. 15/849,770 filed Dec. 21, 2017, which is a continuation of U.S. patent application Ser. No. 15/321,042 filed Dec. 21, 2016, which is a 371 of International Application PCT/IB2015/054792 filed Jun. 25, 2015 which claims priority to U.S. Provisional Application No. 62/017,406 filed Jun. 26, 2014 which is incorporated herein in its entirety.

FIELD OF THE DISCLOSURE

The present disclosure relates to mdm2 inhibitors for use in specific dosing schedules.

BACKGROUND OF THE DISCLOSURE

The protein p53 is a transcription factor that controls the expression of a multitude of target genes involved in DNA damage repair, apoptosis and cell cycle arrest, which are all important phenomena counteracting the malignant growth of tumors. p53 is thus critical for maintaining genetic stability and preventing tumor development. The TP53 gene is one of the most frequently mutated genes in human cancers. It is reported that approximately half of all cancers have inactivated p53, caused by direct mutation. In cancers in which the p53 gene is not mutated, functional inactivation at the protein level has been demonstrated. One of the mechanisms of p53 inactivation described is through its interaction with human homolog of MDM2 (Mouse double minute 2). Mdm2 is therefore an important negative regulator of the p53 tumor suppressor. Mdm2 protein functions both as an E3 ubiquitin ligase, that leads to proteasomal degradation of p53, and an inhibitor of p53 transcriptional activation. Often Mdm2 is found amplified in p53 wild-type tumors.

Mdm2 inhibitors have been developed that inhibit p53-mdm2 interaction and can elicit antineoplastic effect.

US2013/0245089 disclosed a method of treating a patient suffering with cancer by administering to the patient 4-{[(2R,3S,4R,5S)-4-(4-Chloro-2-fluoro-phenyl)-3-(3-chloro-2-fluoro-phenyl)-4-cyano-5-(2, 2-dimethyl-propyl)-pyrrolidine-2-carbonyl]-amino}-3-methoxy-benzoic acid in an amount of from about 800 to about 3000 mg/day for an administration period of up to about 7 days, on days 1-7, of a 28 day treatment cycle, followed by a rest period of from about 21 to about 23 days.

A paper in Clinical Cancer Research by B. Higgins et al. (May 2014) disclosed a 28-day cycle schedule, where RG7388 is administered once weekly three times followed by 13 days of rest (28-day cycle schedule), or where the drug is administered for 5 consecutive days of a 28-day schedule.

Mdm2 inhibitors and how to prepare them were disclosed for example in WO2013111105 or WO2011076786.

SUMMARY OF THE DISCLOSURE

It has been unexpectedly discovered that an advantageous dosing regimen for a Mdm2 inhibitor (hereinafter "Mdm2i") can be designed by understanding the biology of the drug target and how the Mdm2i concentration can alter signaling of the downstream pathway to affect anti-tumor efficacy and tolerability. Surprisingly, it was found that if a sufficiently potent Mdm2i or, in alternative, a sufficiently high dose of a Mdm2i is used, it can cause antineoplastic effect by triggering much longer lasting antiproliferative mechanism in cells. When a cancer cell is exposed to sufficiently high concentration of the respective Mdm2i for as short as 8 hours (and proportionally longer if a lower concentration is used), Mdm2i causes p21 and Puma mRNA expression to spike within the next 48 to 72 hours, leading to significant induction of caspase 3/7 activity and thus to substantial apoptosis. In animals that have had cancer cells implanted subcutaneously the same effect after treating the animal with a sufficiently high single dose was observed. This led to substantial tumor shrinkage. None of this was detected when the Mdm2i exposure was below a certain threshold below which this second modality of Mdm2i was not activated. The knowledge of the second modality of Mdm2i can help plan clinical trials in a way to reduce side effects due to an on-target effect of the drug.

Interestingly, it was observed that a long lasting effect can be sustained for several weeks after a single dose, which eliminates the need for daily treatment and allows administering the drug intermittently. During the breaks with no administration of a drug an organism can recover from potential on-target effects or side effects; particularly numbers of white blood cells (WBC), neutrophils and platelets can recover. Administering the Mdm2i at doses that trigger the long lasting effect causes the Mdm2i to be at least as effective as when dosed daily at lower doses, and can be better tolerated. Less frequent dosing can also lead to better patient friendliness, patient compliance, and particularly where the drug is administered intravenously, can have significant patient benefits. For example, the local injection site irritations can properly heal before the next dose is due.

The intermittent dosing of an Mdm2i with a sustained effect can be combined with a dosing regimen comprising a daily administration of a lower dose compared to the dose used to achieve a sustained effect. The combination of intermittent dosing of a first dose and daily dosing of a second dose yields synergistic effect in terms of the compound efficacy, which is observed for example as a tumor shrinkage or tumor regression. In addition, due to better tolerability of Mdm2i when administered intermittently, the drug can be used in combination with other antineoplastic agents. The combination of a Mdm2i and another antineoplastic agent can exploit improved tolerability of the Mdm2i when it is dosed intermittently, while increasing the overall efficacy of the combination therapy with a second antineoplastic agent.

Specifically, the present disclosure provides the following aspects, advantageous features and specific embodiments, respectively alone or in combination, as listed in the following items:

1. A MDM2i for use in the treatment of cancer, wherein MDM2i is administered to a subject intermittently in at least three consecutive doses and the period between each two consecutive doses is at least 2 weeks.

2. The MDM2i for use in the treatment of cancer according to item 1, wherein MDM2i is administered to a subject intermittently and the period between each two consecutive administrations is at least 3 weeks and not longer than 60 days.

3. The MDM2i for use in the treatment of cancer according to item 1 or 2, wherein MDM2i is administered to a subject intermittently and the period between consecutive administrations is 3 weeks.

4. The MDM2i for use in the treatment of cancer according to any one of items 1 to 3, wherein MDM2i is administered intravenously.

5. A MDM2i for use in the treatment of cancer, wherein MDM2i is administered to a subject in a first and a second dose and the first dose is administered on the same day as the second dose, consecutive days or a different day to the second dose, wherein two consecutive administrations of the first dose are administered intermittently at least every 1 week, 2 weeks, 3 weeks, 4 weeks, 6 weeks or every 60 days, and not longer than every 60 days, and the first and the second dose are not the same.

6. The MDM2i for use in the treatment of cancer according to item 5, wherein the second dose is administered daily, optionally with a break.

7. The MDM2i for use in the treatment of cancer according to item 6, wherein the break is at least 1 day long, 2 days, 3 days, 4 days, 1 week, 2 weeks, or 3 weeks and at most 26 days long.

8. The MDM2i for use in the treatment of cancer according to any one of items 5 to 7, wherein the second dose is administered 1 to 14 days after the first dose has been administered.

9. The MDM2i for use in the treatment of cancer according to any one of items 5 to 8, wherein the second dose is administered for two weeks followed by a period of two weeks without treatment and then repeating the cycle.

10. The MDM2i for use in the treatment of cancer according to any one of items 5 to 9, wherein the first dose is higher than the second dose.

11. The MDM2i for use in the treatment of cancer according to any one of items 5 to 10, wherein at least one of the first or the second dose is administered intravenously.

12. The MDM2i for use in the treatment of cancer according to any one of items 5 to 11, wherein two consecutive administrations of the first dose are administered intermittently at least every 2 weeks.

13. The MDM2i for use in the treatment of cancer according to any one of items 5 to 11, wherein two consecutive administrations of the first dose are administered intermittently at least every 3 weeks.

14. The MDM2i for use in the treatment of cancer according to any one of items 1 to 13, wherein the cancer is bladder, breast, brain, head and neck, liver, oral, biliary tract, acute and chronic lymphoid leukemia, acute and chronic myeloid leukemia, chronic myelomonocytic leukemia, colorectal, gastric, gastrointestinal stromal, hepatocellular, glioma, lymphoma, melanoma, multiple myeloma, myeloproliferative disease, neuroendocrine, lung, non-small cell lung, pancreatic, ovarian, prostate, renal cell, sarcoma, liposarcoma and thyroid cancer.

15. The MDM2i for use in the treatment of cancer according to any one of items 1 to 13, wherein the cancer is melanoma, lung cancer or neuroblastoma.

16. The MDM2i for use in the treatment of cancer according to any one of items 1 to 13, wherein the cancer is melanoma.

17. Use of a MDM2i for the preparation of a medicament for the treatment of a cancer, wherein MDM2i is administered intermittently in at least three consecutive doses and the period between each two consecutive doses is at least 2 weeks, at least 3 weeks, at least 4 weeks, at least 6 weeks or 60 days, and not longer than 60 days.

18. A method of treating cancer, wherein MDM2i is administered to a subject in need thereof intermittently in at least three consecutive doses and the period between each two consecutive doses is at least 2 weeks, 3 weeks, at least 4 weeks, at least 6 weeks or 60 days, and not longer than 60 days.

19. The MDM2i for use in the treatment of cancer according to any one of items 1 to 16, the use of a MDM2i for the preparation of a medicament for the treatment of a cancer according to item 17, or the method of treating cancer according to item 18, wherein MDM2i is administered to a human.

20. The MDM2i for use in the treatment of cancer according to any one of items 1 to 16, or 19, the use of a MDM2i for the preparation of a medicament for the treatment of a cancer according to item 17 or 19, or the method of treating cancer according to item 18 or 19, wherein the MDM2i is selected from the group consisting of:

(S)-1-(4-Chloro-phenyl)-7-isopropoxy-6-methoxy-2-(4-{methyl-[4-(3-oxo-piperazin-1-yl)-trans-cyclohexylmethyl]-amino}-phenyl)-1,4-dihydro-2H-isoquinolin-3-one (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one (S)-1-(4-Chloro-phenyl)-7-isopropoxy-6-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one (S)-1-(4-Chloro-phenyl)-7-isopropoxy-6-methoxy-2-(6-{methyl-[4-(3-methyl-4-oxo-imidazoidin-1-yl)-trans-cyclohexylmethyl]-amino}-pyridin-3-yl)-1,4-dihydro-2H-isoquinolin-3-one (S)-1-(4-Chloro-phenyl)-7-isopropoxy-6-methoxy-2-(5-{methyl-[4-(3-methyl-4-oxo-imidazolidin-1-yl)-trans-cyclohexylmethyl]-amino}-pyrazin-2-yl)-1,4-dihydro-2H-isoquinolin-3-one 1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one, (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile (S)-5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one (S)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one,

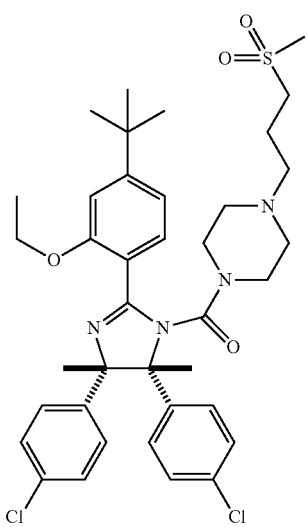
RG7112
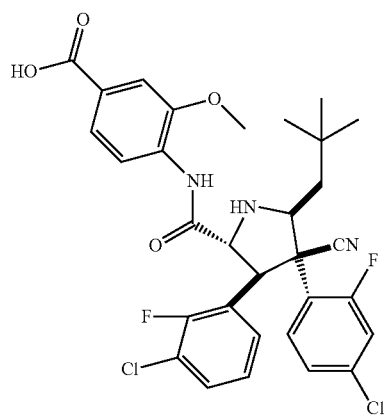
RG738
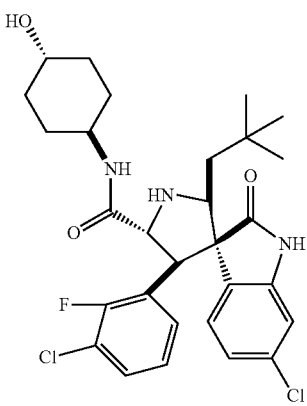
SAR299155
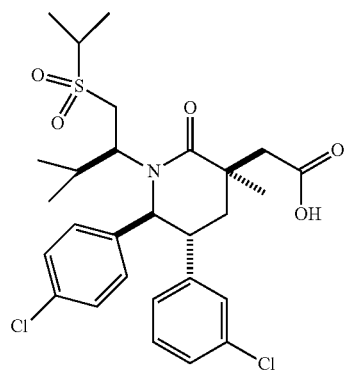
AMG 232
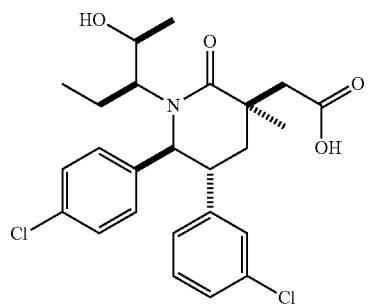
AM-8553
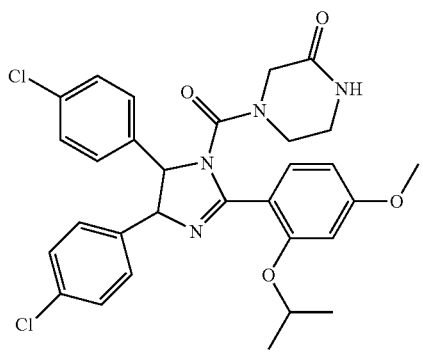
Nutlin-3
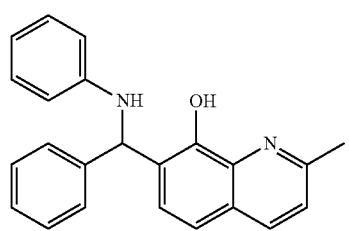
NSC 66811

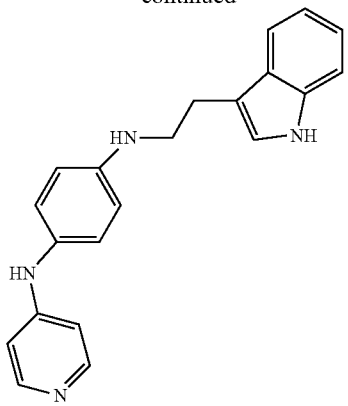

JNJ-26854165 and
(S)-5-(5-chloro-1-methyl-2-oxo-1,2-dihydropyridin-3-yl)-6-(4-chlorophenyl)-2-(2,4-dimethoxy-d6-pyrimidin-5-yl)-1-((R)-1-methoxypropan-2-yl)-5,6-dihydropyrrolo[3,4-d]imidazol-4(1H)-one.

21. The MDM2i for use in the treatment of cancer according to any one of items 1 to 16, or 19, the use of a MDM2i for the preparation of a medicament for the treatment of a cancer according to item 17 or 19, or the method of treating cancer according to item 18 or 19, wherein the MDM2i is
(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one or
(S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one.

22. The MDM2i for use in the treatment of cancer according to any one of items 1 to 16, or 19, the use of a MDM2i for the preparation of a medicament for the treatment of a cancer according to item 17 or 19, or the method of treating cancer according to item 18 or 19, wherein the MDM2i is (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one.

23. The MDM2i for use in the treatment of cancer according to any one of items 1 to 16, or 19 to 22, the use of a MDM2i for the preparation of a medicament for the treatment of a cancer according to any one of items 17 or 19 to 22, or the method of treating cancer according to item 18 or 19 to 22, wherein the MDM2i for use in the treatment of cancer, the use of a MDM2i for the preparation of a medicament or the method of treating cancer further comprise another pharmaceutical ingredient which is administered to a patient.

24. The MDM2i for use in the treatment of cancer according to item to 23, the use of a MDM2i for the preparation of a medicament for the treatment of a cancer according to item to 23, or the method of treating cancer according to item to 23, wherein the another pharmaceutical ingredient is another antineoplastic agent.

25. The MDM2i for use in the treatment of cancer according to item to 24 the use of a MDM2i for the preparation of a medicament for the treatment of a cancer according to item to 24, or the method of treating cancer according to item to 24, wherein more than one further antineoplastic agent is administered.

26. The MDM2i for use in the treatment of cancer according to any one of items 23 to 25, the use of a MDM2i for the preparation of a medicament for the treatment of a cancer according to any one of items 23 to 25, or the method of treating cancer according to any one of items 23 to 25, wherein MDM2i is administered intermittently in at least three consecutive doses and the period between each two consecutive doses is at least 1 week.

27. The MDM2i for use in the treatment of cancer according to any one of items 23 to 25, the use of a MDM2i for the preparation of a medicament for the treatment of a cancer according to any one of items 23 to 25, or the method of treating cancer according to any one of items 23 to 25, wherein MDM2i is administered intermittently in at least three consecutive doses and the period between each two consecutive doses is at least 2 weeks.

28. The MDM2i for use in the treatment of cancer according to any one of items 23 to 25, the use of a MDM2i for the preparation of a medicament for the treatment of a cancer according to any one of items 23 to 25, or the method of treating cancer according to any one of items 23 to 25, wherein MDM2i is administered intermittently in at least three consecutive doses and the period between each two consecutive doses is at least 3 weeks.

29. The MDM2i for use in the treatment of cancer according to any one of items 1 to 16, or 19 to 28, the use of a MDM2i for the preparation of a medicament for the treatment of a cancer according to any one of items 17 or 19 to 28, or the method of treating cancer according to item 18 or 19 to 28, wherein the MDM2i is (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one.

30. The MDM2i for use in the treatment of cancer according to any one of items 1 to 16, or 19 to 28, the use of a MDM2i for the preparation of a medicament for the treatment of a cancer according to any one of items 17 or 19 to 28, or the method of treating cancer according to item 18 or 19 to 28, wherein the MDM2i is (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one.

The term "Mdm2 inhibitor" or "Mdm2i" denotes herein any compound inhibiting the HDM-2/p53 or HDM-4/p53 interaction with an $IC_{50}$ of less than 10 μM, preferably less than 1 μM, preferably in the range of nM, measured by a Time Resolved Fluorescence Energy Transfer (TR-FRET) Assay. The inhibition of p53-Hdm2 and p53-Hdm4 interactions is measured by time resolved fluorescence energy transfer (TR-FRET). Fluorescence energy transfer (or Foerster resonance energy transfer) describes an energy transfer between donor and acceptor 5 fluorescent molecules. For this assay, MDM2 protein (amino acids 2-188) and MDM4 protein (amino acids 2-185), tagged with a C-terminal Biotin moiety, are used in combination with a Europium labeled streptavidin (Perkin Elmer, Inc., Waltham, Mass., USA) serving as the donor fluorophore. The p53 derived, Cy5 labeled peptide Cy5-TFSDLWKLL (p53 aa18-26) is the energy acceptor. Upon excitation of the donor 10 molecule at 340 nm, binding interaction between MDM2 or MDM4 and the p53 peptide induces energy transfer and enhanced response at the acceptor emission wavelength at 665 nm. Disruption of the formation of the p53-MDM2 or p53-MDM4 complex due to an inhibitor molecule binding to the p53 binding site of MDM2 or MDM4 results in increased donor emission at 615 nm. The ratiometric FRET assay readout is calculated from the 15 raw data of the two distinct fluorescence signals measured in time resolved mode (countrate 665 nm/countrate 615 nm×1000). The assay can be performed according to the following procedure: The test is performed in white 1536w microtiterplates (Greiner Bio-One GmbH, Frickenhausen, Germany) in a total volume of 3.1 μl by combining 100 nl of compounds diluted in 90% DMSO/10% H2O (3.2% final DMSO concentration) with 2 μl Europium 20 labeled streptavidin (final concentration 2.5 nM) in reaction buffer (PBS, 125 mM NaCl, 0.001% Novexin (consists of carbohydrate polymers (Novexin polymers), designed to increase the solubility and stability of proteins; Novexin Ltd., ambridgeshire, United Kingdom), Gelatin 0.01%, 0.2% Pluronic (block copolymer from ethylenoxide and propyleneoxide, BASF, Ludwigshafen, Germany), 1 mM DTT), followed by the addition of 0.5 μl MDM2-Bio or MDM4-Bio diluted in assay buffer (final concentration 10 nM). Allow the solution to pre-incubate for 15 minutes at room temperature, followed by addition of 0.5 μl Cy5-p53 peptide in assay buffer (final concentration 20 nM). Incubate at room temperature for 10 minutes prior to reading the plate. For measurement of samples, an Analyst GT multimode microplate reader (Molecular Devices) with the following settings 30 is used: Dichroic mirror 380 nm, Excitation 330 nm, Emission Donor 615 nm and Emission Acceptor 665 nm. IC50 values are calculated by curve fitting using XLfit. If not specified, reagents are purchased from Sigma Chemical Co, St. Louis, Mo., USA.

According to one embodiment, a Mdm2 inhibitor can be for example a compound of any of the following formulas:
S)-1-(4-Chloro-phenyl)-7-isopropoxy-6-methoxy-2-(4-{methyl-[4-(3-oxo-piperazin-1-yl)-trans-cyclohexylmethyl]-amino}-phenyl)-1,4-dihydro-2H-isoquinolin-3-one
(S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one
(S)-1-(4-Chloro-phenyl)-7-isopropoxy-6-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one
(S)-1-(4-Chloro-phenyl)-7-isopropoxy-6-methoxy-2-(6-{methyl-[4-(3-methyl-4-oxo-imidazolidin-1-yl)-trans-cyclohexylmethyl]-amino}-pyridin-3-yl)-1,4-dihydro-2H-isoquinolin-3-one
(S)-1-(4-Chloro-phenyl)-7-isopropoxy-6-methoxy-2-(5-{methyl-[4-(3-methyl-4-oxo-imidazolidin-1-yl)-trans-cyclohexylmethyl]-amino}-pyrazin-2-yl)-1,4-dihydro-2H-isoquinolin-3-one
1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one,
(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one
4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile
(S)-5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one
(S)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one,

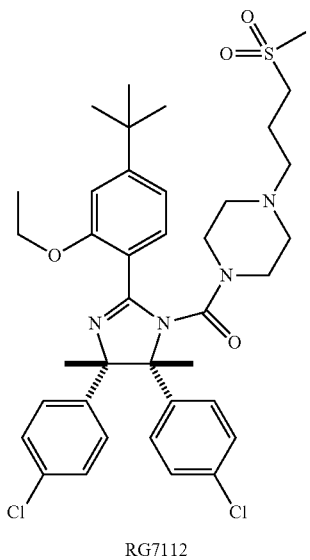

RG7112

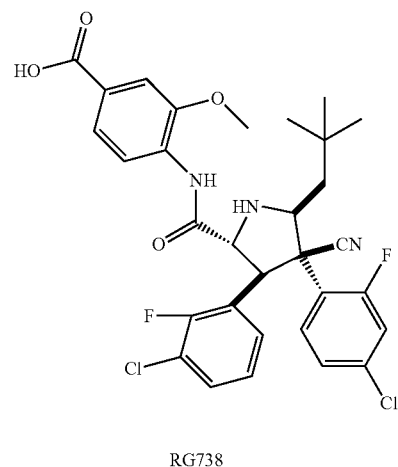

RG738

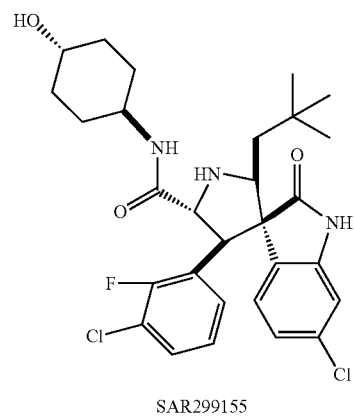

SAR299155

-continued

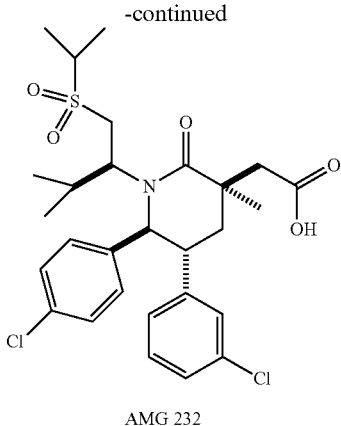

AMG 232

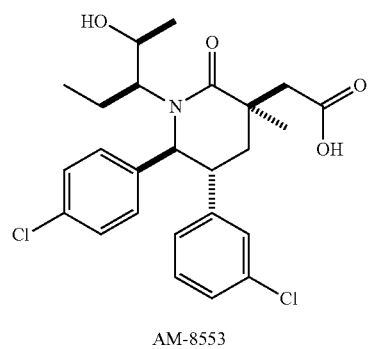

AM-8553

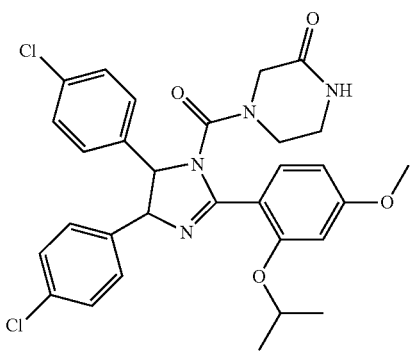

Nutlin-3

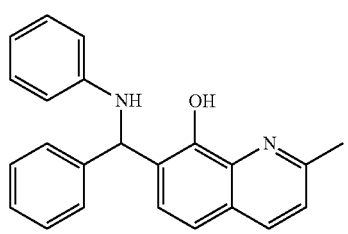

NSC 66811

-continued

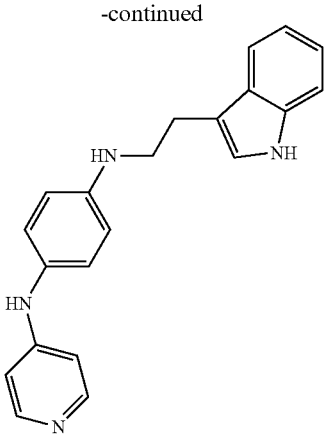

JNJ-26854165 or
(S)-5-(5-chloro-1-methyl-2-oxo-1,2-dihydropyridin-3-yl)-6-(4-chlorophenyl)-2-(2,4-dimethoxy-d6-pyrimidin-5-yl)-1-((R)-1-methoxypropan-2-yl)-5,6-dihydropyrrolo[3,4-d]imidazol-4(1H)-one.

In a particular embodiment, the MDM2i is (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one (hereinafter compound A), or a pharmaceutically acceptable salt thereof.

In another embodiment, the MDM2i is (S)-1-(4-Chlorophenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one (hereinafter compound B).

The term "subject" or "patient" as used herein includes animals, which are capable of suffering from or afflicted with a cancer or any disorder involving, directly or indirectly, a cancer. Examples of subjects include mammals, e.g., humans, dogs, cows, horses, pigs, sheep, goats, cats, mice, rabbits, rats and transgenic non-human animals. In the preferred embodiment, the subject is a human, e.g., a human suffering from, at risk of suffering from, or potentially capable of suffering from cancer. In a particular embodiment, subject or patient is human.

The term "treating" or "treatment" as used herein denotes to arrest, delay the onset (i.e., the period prior to clinical manifestation of a disease) and/or reduce the risk of developing or worsening a disease, or comprises relieving, reducing or alleviating at least one symptom in a subject or effecting a delay of progression of a disease. For example, treatment can be the diminishment of one or several symptoms of a disorder or complete eradication of a disorder, such as cancer.

The term "antineoplastic agent" is a pharmaceutical active ingredient that exhibits antiproliferative or anti-cancer activity. Possible antineoplastic agents suitable for combination treatment include, but are not limited to BRAF inhibitors (e.g. (S)-methyl-1-(4-(3-(5-chloro-2-fluoro-3-(methylsulfonamido)phenyl)-1-isopropyl-1H-pyrazol-4-yl)pyrimidin-2-ylamino)propan-2-ylcarbamate or vemurafenib); anaplastic lymphoma kinase (ALK) inhibitors (e.g. ceritinib, AE684, Alectinib, Crizotinib, AP26113, ASP3026, ADZ3463); aromatase inhibitors (e.g. atame-stane, exemestane and formestane, aminoglutethimide, roglethimide, pyridoglutethimide, trilostane, testolactone, ketoconazole, vorozole, fadrozole, anastrozole or letrozole); antiestrogens (tamoxifen, fulvestrant, raloxifene or raloxifene hydrochloride); antiandrogen (e.g. bicalutamide); topoisomerase I inhibitors (e.g. topotecan, gimatecan, irinotecan, camptothecian and its analogues, 9-nitrocamptothecin and the macromolecular camptothecin conjugate PNU-166148 (compound A1 in WO99/17804); topoisomerase II inhibitors (e.g. doxorubicin, dauno-rubicin, epirubicin, idarubicin, nemorubicin, mitoxantrone, losoxantrone, etoposide or teniposide); microtubule active compounds (e.g. paclitaxel, docetaxel, vinblastine, vinblastine sulfate, vincristine, vincristine sulfate, vinorelbine, discodermolides, cochicine); alkylating compounds (e.g. cyclophosphamide, ifosfamide, melphalan or nitrosourea); histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity; anti-angiogenic compounds; compounds which target, decrease or inhibit the activity of a protein or lipid phosphatase; gonadorelin agonists (e.g. abarelix, goserelin and goserelin acetate); methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Ft-3; Hsp90 inhibitors; kinesin spindle protein inhibitors; MEK inhibitors; leucovorin; EDG binders; antileukemia compounds; ribonucleotide reductase inhibit-tors; S-adenosylmethionine decarboxylase inhibitors; angiostatic steroids; corticosteroids; other chemotherapeutic compounds (as defined below); photosensitizing compounds (e.g. VISUDYNE and porfimer sodium).

DETAILED DESCRIPTION OF THE DISCLOSURE

Figure 1:
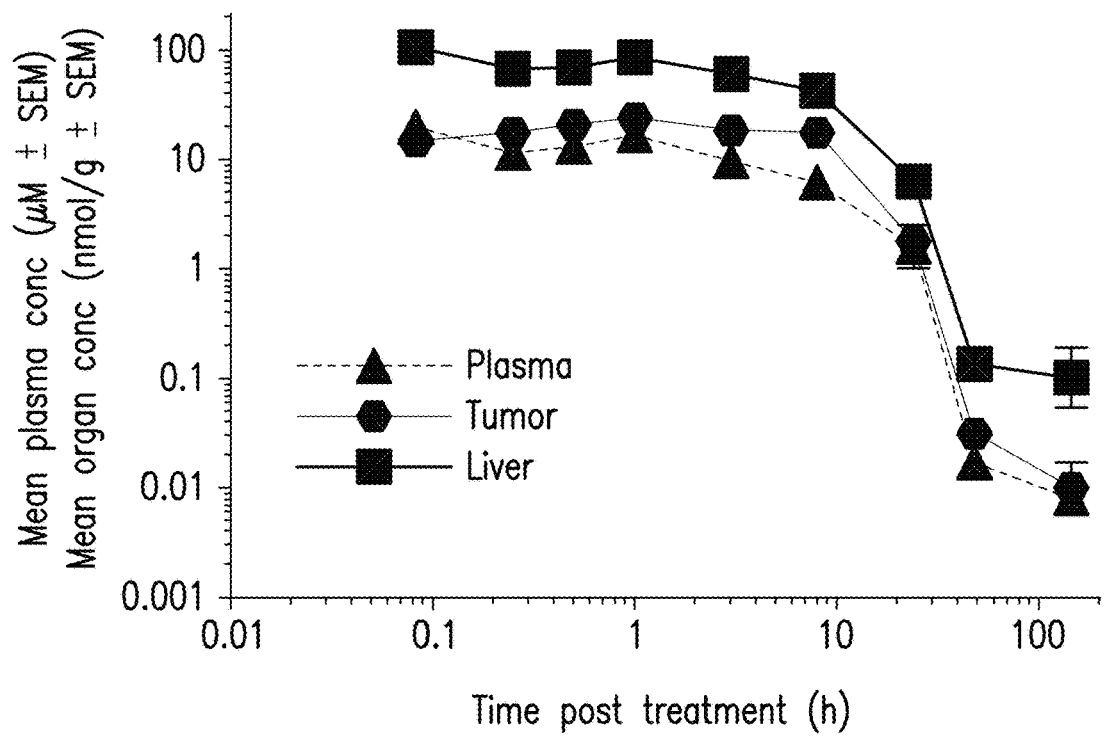
FIG. 1 depicts the PK of Compound A on SJSA-1 tumor-bearing rat after one single intravenous (i.v.) treatment

Currently, Mdm2 inhibitors are dosed daily, optionally with drug holidays. The break after a series of daily treatments with Mdm2i may have been extended in certain cases due to tolerability issues. Exceptionally, Mdm2 inhibitors are dosed at weekly intervals. Now, it was found that (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one (compound A) in a higher single dose administered intravenously or per os allowed for the first time a strong Puma mRNA induction (Emax≥70 fold induction) which was never reached previously with a lower per os (p.o.) dose of compound A or (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one (compound B). It is interesting to note that Mdm2, the inhibitor of p53, had the lowest mRNA induction. Such high Puma mRNA induction in the tumor was followed by a strong caspase-3 activation 24 h post-treatment which translated in a dramatic decrease in tumor cell density 48 and 72 h post-treatment. The strong induction of the apoptotic pathway was clearly identified as the main driver of the striking and unexpected tumor regression induced by a single treatment at high dose. Indeed, single i.v. treatment with compound A at 20 mg/kg induced a complete SJSA-1 tumor response (100% regression) in 82% (9/11) of treated rat for 42 days. Moreover, once every 3 weeks (q3w) p.o. treatment with compound A at 27 mg/kg induced an 88 and 27% SJSA-1 tumor regression after one and two cycles, respectively.

We found that in order to trigger prolonged apoptosis or sustained antiproliferative effect with strong Puma induction (i.e. at least 20 fold induction of mRNA expression compared to the mRNA expression in non-treated cancer cells) compound A has to be administered at a sufficiently high dose. Said dose allows the drug to be administered intermittently without significantly losing efficacy and potentially improving tolerability. Single doses of Compound A can be dosed every 2 weeks. Also breaks of 3 weeks, 4 weeks, 6 weeks, or even intermittence of 60 days can still show significant effect on the tumor. Below said high dose, compound A only induces Puma mRNA expression up to about 5-6 fold and as a consequence requires to be administered continuously, for example daily, in order to attain a continuous antiproliferative effect. Once the drug has been administered long enough, even at lower dose, a break from treatment can be made, but the treatment cycle has to be repeated in at least about 2 weeks, otherwise the antiproliferative effect is not observed anymore.

In one embodiment, according to the present disclosure, Mdm2i used for the treatment of cancer is provided, wherein a single dose of the Mdm2i is to be administered at least every two weeks, and not longer than every 60 days. In another embodiment, the single dose of the Mdm2i is to be administered at least every three weeks, and not longer than every 60 days.

Other Mdm2i than compound A can also achieve strong Puma induction, but the dose to be used is dependent on the compound's potency. Without wanting to be bound to any theory, it is believed that the dose of a Mdm2i to generate a prolonged effect via very pronounced Puma induction needs to be lower when the Mdm2i is more potent. But in principle also low potent Mdm2i can activate this second level modality that leads to long-lasting effect, if only administered at a dose that reaches sufficient plasma exposure. About 26% tumor regression can be achieved if the Mdm2i is above the GI80-concentration for at least 8 hours, and of more than 90% if the Mdm2i exposure persists above GI80 for at least 17 hours. GI-80 is the dose necessary to cause 80% of tumor cell growth inhibition. Therefore, generally, the high dose or higher dose of a Mdm2i is the dose that causes the Mdm2i to persist for at least 8 hours, preferably at least 10 hours, in plasma in vivo at least at a concentration that otherwise causes GI-80 when exposing the tumor cells in vitro to the Mdm2i for 8 hours. GI-80 concentration can be measured by any proliferation test. For example, CellTiter-Glo® Luminescent Cell Viability Assay is used. For example cells in vitro are treated with the Mdm2i for 8 hours, then the cells are washed to remove the compound in the medium and determination of the number of viable cells is made after 72 hours. This is repeated with various concentrations to identify GI-80 concentration. The high dose has to reach or supersede in vivo said GI-80 concentration of the Mdm2i for at least 8 hours. Low dose is lower than the lowest high dose. Unfortunately, administering higher doses of Mdm2i does not always translate into sufficient plasma exposure simply due to specific pharmacokinetics of the compound, particularly if given orally, because for example low bioavailability can prevent the drug from achieving sufficiently high plasma levels. This drawback of oral administration is overcome when the Mdm2i is administered intravenously.

The "dose" as mentioned herein in the context of an administered dose can also mean strength.

Thus, it is one objective of this disclosure to provide a MDM2i for use in the treatment of cancer, wherein MDM2i is to be administered to a subject intermittently and the period between at least three consecutive doses is at least 2 weeks, at least 3 weeks, at least 4 weeks, at least 6 weeks or 60 days, and not longer than 60 days. MDM2i is to be administered to a subject intermittently in at least three consecutive doses and the period between each two consecutive doses of the three doses is at least 2 weeks, at least 3 weeks, at least 4 weeks, at least 6 weeks or 60 days. The upper limit is set based on the available data, but we allow for a possibility, that even more infrequent administration may lead to clinically acceptable outcome and could be useful. To improve patient compliance, the administration regimen for the Mdm2i can be once every 3 weeks or 4 weeks, particularly once every 3 weeks.

We found that the problem of suboptimal exposure of the Mdm2i in a body, particularly if it has cell proliferation IC50 of more than 1 μM, can be solved by administering the drug intravenously. As an example, we found that lower doses of compound A (20 mg/kg) can be administered intravenously, while 27 mg/kg were needed orally to stimulate the same response. Therefore, administering Mdm2i intravenously opens a chance for Mdm2i of a lower potency to achieve the aforementioned second stage of reactivity with extended antiproliferative effect. This way, there is a chance to dose the drug less frequently, because only intravenous administration will lead to the required exposure. In addition, administering Mdm2i intravenously at a lower dose compared to the dose that would be needed for oral administration can at least offer some tolerability advantage.

Therefore, in one embodiment, we provide Mdm2i for use in the treatment of cancer, wherein MDM2i is to be administered intravenously.

In another embodiment, the intermittent dosing of a MDM2i can be supplemented by another dosing regimen of a second dose of the MDM2i that is different to the dose used in the intermittent dosing of a single dose. Combining the intermittent dosing schedule with another more frequent schedule allows reducing the dose of Mdm2i used in each of the schedules and thus further improves tolerability. Administering a high dose of a Mdm2i intermittently while also dosing the Mdm2i more frequently, e.g. daily at a lower dose enables to reduce doses for both schedules to the level that would otherwise not be efficacious, at least in one of the two dosing schedules, if said dosing schedules was used alone. Combining the treatment with a high and a low dose at different schedules also proved to be synergistically effective. In one embodiment, the intermittent dosing, where Mdm2i is administered at least every 2 weeks, daily treatment of the Mdm2i can be superimposed. We found that combining two dosing regimens of compound A, namely the treatment once every 3 weeks with a higher dose and a 2 week daily treatment with a lower dose with a 2-week break every 28-day cycle, lead to synergistic antitumor effect of both treatments. The second dosing regimen that is added to the intermittent treatment can start on the same, consecutive or other day. The second dosing regimen can be for example daily, optionally with a break. The break after a series of daily treatments can be at least 1 day long, 2 days, 3 days, 4 days, 1 week, 2 weeks, or 3 weeks and at most 26 days long. In one embodiment, the dose of the second dosing regimen is to be administered 1 to 14 days after the first dose has been administered. In a specific embodiment, the second dosing schedule with a lower dose of Mdm2i starts on the next day after single high dose has been administered. The dose that is administered daily can be administered for two weeks followed by a period of two weeks without treatment and then the treatment cycle can be repeated. Generally, the dose used for intermittent dosing will be higher than the second dose used in more frequent dosing that is added to the intermittent dosing. Mdm2i can be administered either per os or intravenously, or in combination thereof. For example, intermittent dose at least every 2, 3, 4, 6 weeks or 60 days can be administered intravenously, whereas the second daily dose can be given orally. However, both doses can be administered intravenously, or both orally. In one embodiment, the first dose that is administered intermittently can be administered with periods between two consecutive administrations of at least 2 weeks.

In one aspect, the second dosing schedule that is added to the intermittent dosing schedule can comprise administering the Mdm2i for a period of at least 5 days followed by a period of 1 day or more, and repeating the cycle while the patient is treated with the Mdm2i intermittently at the different dose. However, additional second dosing schedules include, for example, cycles of 2 weeks on, 1 or 2 weeks off; 3 weeks on 1, 2 or 3 weeks off; 4 weeks on 1, 2, 3 or 4 weeks off; 1 week on, 3 weeks off; 3 weeks on, 1 weeks off; 4 weeks on, 1 week off.

In addition of adding a second dosing schedule to the intermittent dosing, a clinical outcome of a MDM2i treatment with the intermittent dosing can be improved by administering a further pharmaceutical ingredient to the subject. The further pharmaceutical ingredient can be another Mdm2i, but most often it will be a drug with a different mechanism of action. It is contemplated herein that giving another antineoplastic agent in addition to intermittently dosed Mdm2i can achieve improved antitumor effect. In addition, intermittent dosing opens up more flexibility to combining Mdm2i with another antineoplastic agent as by reducing the frequency of Mdm2i dosing, tolerability can improve and thus allows more options to add another anticancer drug. In one embodiment, the Mdm2i is administered intermittently as described herein in combination with a BRAF inhibitor or an ALK inhibitor. Specifically, the another pharmaceutical ingredient is (S)-methyl-1-(4-(3-(5-chloro-2-fluoro-3-(methylsulfonamido)phenyl)-1-isopropyl-1H-pyrazol-4-yl)pyrimidin-2-ylamino)propan-2-ylcarbamate. In another embodiment, the combination is made with Ceritinib. Where the Mdm2i is combined with another pharmaceutical ingredient, the Mdm2i can be administered intermittently with the periods between single doses being at least 1 week, at least 2 weeks, at least 3 weeks, at least 4 weeks, at least 6 weeks or 60 days, and not longer than 60 days.

The present disclosure provides also compound A for use in the treatment, wherein the compound A is administered intermittently, e.g. the period between each two doses of at least three doses is at least 1 week, at least 2 weeks, at least 3 weeks, at least 4 weeks, at least 6 weeks or 60 days, and not longer than 60 days, and (S)-methyl-1-(4-(3-(5-chloro-2-fluoro-3-(methylsulfonamido)phenyl)-1-isopropyl-1H-pyrazol-4-yl)pyrimidin-2-ylamino)propan-2-ylcarbamate or Ceritinib are also used. Particularly, the compound A is administered as a single dose at least every week, or at least every three weeks.

The Mdm2i and additional pharmaceutical ingredient can be applied or formulated of the separate partners with or without, preferably with, instructions for combined use or to combination products. The compounds in the combination may thus be administered entirely separately or be entirely separate pharmaceutical dosage forms. The combination partners may be pharmaceutical compositions that are also sold independently of each other and where just instructions for their combined use are provided in the package equipment, e.g. leaflet or the like, or in other information e.g. provided to physicians and medical staff (e.g. oral communications, communications in writing or the like), for simultaneous or sequential use for being jointly active. The Mdm2i and another active pharmaceutical ingredient can be provided as a fixed or a non-fixed combination of the active ingredients. The term "fixed combination" means that the active ingredients, e.g. a Mdm2 inhibitor and an antineoplastic agent, are both administered to a patient simultaneously in the form of a single entity or dosage. In other terms: the active ingredients are present in one dosage form, e.g. in one tablet or in one capsule. The term "non-fixed combination" means that the active ingredients are both administered to a patient as separate entities either simultaneously, concurrently or sequentially with no specific time limits, wherein such administration provides therapeutically effective levels of the two compounds in the body of the patient.

The cancers treated by the use of Mdm2i as described herein include cancer such as, but not limited to, bladder, breast, brain, head and neck, liver, oral, biliary tract, acute and chronic lymphoid leukemia, acute and chronic myeloid leukemia, chronic myelomonocytic leukemia, colorectal, gastric, gastrointestinal stromal, hepatocellular, glioma, lymphoma, melanoma, multiple myeloma, myeloproliferative disease, neuroendocrine, lung, non-small cell lung, pancreatic, ovarian, prostate, renal cell, sarcoma, liposarcoma and thyroid cancer. In a specific embodiment, the cancer is melanoma. In another embodiment the cancer is neuroblastoma. In yet another embodiment, the cancer is leukemia.

Based on the data obtained with the Compound A, and knowing also the biochemical response of (S)-1-(4-Chlorophenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one (Compound B), we can expect that the proposed dosing regiments could be used to provide advantageous efficacy or tolerability with at least the Mdm2i listed above.

Mdm2i can be delivered to the subject in a pharmaceutical composition. Oral dosage forms to be used are for example tablets, capsules, sachets, micropellets, granules or the like. The oral dosage forms can comprise in addition to the Mdm2i further conventional carriers or excipients used for pharmaceuticals. Examples of such carriers or excipients include, but are not limited to, disintegrants, binders, lubricants, glidants, stabilizers, and fillers, diluents, colorants, flavours and preservatives. One of ordinary skill in the art may select one or more of the aforementioned carriers with respect to the particular desired properties of the dosage form by routine experimentation and without any undue burden. The amount of each carriers used may vary within ranges conventional in the art. The following references disclose techniques and excipients used to formulate oral dosage forms. See *The Handbook of Pharmaceutical Excipients*, 4th edition, Rowe et al., Eds., American Pharmaceuticals Association (2003); and *Remington: the Science and Practice of Pharmacy*, 20th edition, Gennaro, Ed., Lippincott Williams & Wilkins (2003). The dosage forms are prepared for example by blending, granulating, compressing, compacting, filling, sieving, mixing and/or tableting.

The Mdm2i can be applied in vivo intravenously, e.g. as a solution. Generally, the dosage form would be autoclaved or sterilized by using other process before administration. The drug can be administered intravenously by injection or infusion. Preferably, the Mdm2i is infused intravenously over a period of less than 3 hours, more preferably in up to 2 hours, particularly in about 1 hour.

Mdm2i can be used for preparation of a medicament, where a dosage form is prepared. The latter can be further packaged and supplemented with a patient information leaflet.

The Mdm2i is administered at the therapeutically effective amount. The term "a therapeutically effective amount" of the Mdm2i refers to an amount of the compound that will elicit the biological or medical response of a subject, for example, ameliorate symptoms, alleviate conditions, slow or delay disease progression, slow down tumor growth, or cause tumor regression, or the like. In one embodiment a therapeutically effective amount in vivo may range depending on the route of administration, between about 0.1-500 mg/kg, or between about 1-100 mg/kg. For example, for compound A, the effective in vivo amount is between 100 and 1500 mg every three weeks, particularly between 100 and 800 mg every three weeks, or between 50 and 600 mg daily, when administered per os. For compound B, the effective amount is between 500 and 4000 mg, particularly between 1500 and 4000 mg, when administered per os. Intravenous doses would need to be lowered accordingly.

The following Examples illustrate the present disclosure.

Method and Materials Used in Examples

Compound A—(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one Compound B—(S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one Cell Culture SJSA-1 osteosarcoma cells (CRL-2098, ATCC) are wild type for p53 and amplified in Mdm2 (16.9 copies, SNP 6.0) but not in Mdm4. They were cultured in RPMI 1640 (#1-41F01-1, AMIMED) supplemented with 10% FCS (#2-01F16-1, AMIMED), 2 mM L-glutamine (#5-10K00-H, AMIMED). Cells were passaged by washing first with Dulbecco's PBS without Ca2+/Mg2+(#3-05F29-1, AMIMED), trypsinising cells with Trypsin 0.05% in PBS with EDTA (#5-51F00-H, AMIMED), centrifuging in the respective culture media, and splitting cells into fresh media at a ratio of 1:8, 2 times per week.

Animals

All the nude rat (Hsd:RH-Fox1$^{rnu}$, Harlan Sprague Dawley; SF480) were allowed to adapt for 4 days and housed in a pathogen-controlled environment (5 mice/Type III cage) with access to food and water ad libitum. Animals were identified with transponders. Studies described in this report were performed according to procedures covered by permit number 1975 issued by the Kantonales Veterinäramt Basel-Stadt and strictly adhered to the Eidgenössisches Tierschutzgesetz and the Eidgenössische Tierschutzverordnung. All experiments were done with 4 to 7 rats. Mice were used for experiments with combinations of compounds.

Tumor Model

Subcutaneous tumors were induced by concentrating 1.0× 10$^7$ SJSA-1 cells in 50% Matrigel® and injecting in the right flank of Harlan nude rats. Efficacy experiment could start 14 days post cell injection. Compound A was made-up fresh for each administration. For i.v. injection (4 ml/kg), Compound A was dissolved in 30% PEG300, 10% Solutol HS 15, 6% Pluronic F68 and 54% water. For per os (p.o.) injection (5 ml/kg), Compound A was dissolved in methylcellulose 0.5% w/V in phosphate buffer pH 6.8 50 mM. The animals were treated either at a high dose (20 mg/kg i.v. or 27 mg/kg p.o.) once every 3 weeks (q3w) or at a high dose (15 mg/kg p.o.) followed 24 h later by a daily low dose treatment (3 mg/kg p.o., 2 weeks on/2 weeks off).

The tumor volume (TVol) and body-weight (BW) of the animal were measured three times per week allowing calculation at any particular time-point relative to the day of initiation of treatment (day 0) of the percentage change in TVol (Δ% TVol). Tumor response was quantified by the change in tumor volume (endpoint minus starting value in mm$^3$) as the T/C i.e.

$$\left(\frac{\Delta TVol_{drug}}{\Delta TVol_{vehicle}} \times 100\right)$$

In the case of a tumor regression or to assess the percentage of change in TVol, the tumor response was quantified by the percentage of regression of the starting TVol, ie $$\left(\frac{\Delta TVol_{drug}}{\Delta TVol_{Day0}} \times 100\right).$$

Similarly, the body-weight (BW) of the animal was measured three times per week allowing calculation at any particular time-point relative to the day of initiation of treatment (day 0) of the percentage change in BW (Δ % BW).

The white blood cells (WBC), neutrophils and platelets were counted using a Sysmex (XT-2000i).

Blood was collected into commercially prepared EDTA coated microtubes (BD Microtainer, cat #365975).

Pharmacokinetic (PK) and Pharmacodynamic (PD)

At the times indicated, animals were anaesthetized by exposure to 2-3% v/v isofluorane in medical oxygen:

Either the animal was killed without recovering from anesthetic after blood sampling. Blood was collected into commercially prepared EDTA coated tubes (Milian, cat #TOM-14C) in order to extract plasma. The tissues were excised, weighed and rapidly frozen in liquid nitrogen.

Or a tumor biopsy was collected by using a biopsy gun and flushing the needle with RLT buffer in Barney rubble tubes (Covaris, cat #520048). In addition, 20 μl of blood may have been collected from the tail vein and diluted in 20 μl of water. After recovery of anesthesia, animals were transferred in their respective cages.

Tissue, blood and plasma samples were stored frozen at −80° C. until analysis.

Preparation of Tissue

Frozen tissues were cryogenic dry pulverized and biopsies were sonicated using the CryoPrep™ system (model CP-02) from Covaris. More specifically, frozen tissues were transferred to disposable tubes called TissueTubes™, placed in the CryoPrep™ system and then pulverized using the appropriate impact setting. The resulting powder was collected with a spatula and weighed for further processing (mRNA purification or quantification of compound in tissues). The biopsies were flushed in a Barney rubble glass tubes with 350 µl of RLT buffer and placed in the Covaris for sonication (1 min per biopsy). The resulting lysate was transferred into a QIAshredder (79654, Qiagen) column for RNA extraction.

Pharmacodynamic (qRT-PCR)

Total RNA was purified from cell pellets using the QIAshredder (79654, Qiagen) and RNeasy Mini Kit (74106, Qiagen) according to the manufacturer's instructions, with the exception that no DNA digestion was performed. Total RNA was eluted with 50 µL of RNase-free water. Total RNA was quantitated using the spectrophotometer ND-1000 Nanodrop®. The qRT-PCR (Quantitative Reverse Transcriptase Polymerase Chain Reaction) was set up in triplicate per sample using the One-Step RT qPCR Master Mix Plus (RT-QPRT-032X, Eurogentec), with either control primers and primers for the target, namely TaqMan Gene Expression assays (20× probe dye FAM™ (or VIC)-TAMRA (or MGB); Applied Biosystems) listed in Table 1.

TABLE 1

Source of qRT-PCR primers

| Gene | Species | TaqMan ® Gene Expression Kit |
|---|---|---|
| GUS beta | Human | 4310888E-1012026 |
| Gapdh | Human | 4310884E-0904043 |
| Cdkn1 a (p21) | Human | Hs00355782_m1 |
| BBC3 (puma) | Human | Hs00248075_m1 |
| Mdm2 | Human | Hs01066930_m1 |

Pharmacokinetic

Sample Preparation and Bioanalytical Method

Concentrations of compound A in plasma and tissues were determined simultaneously by an UPLC/MS-MS assay. Tissues were homogenized in an equal volume of HPLC-Water (Water for chromatography, Merck) using the Fast Prep®-24 system (M.P. Biomedicals, Irvine, Calif., USA). Following addition of 25 µl of internal standard mixture (1 µg/ml) to analytical aliquots (25 µl) of plasma or tissues homogenate the proteins were precipitated by the addition of 200 µl acetonitrile. The supernatant were transferred in a fresh vial. After evaporation to dryness the samples were re-dissolved in 60 µl acetonitrile/water (1/1 v/v). An aliquot (5 µl) of this solution was separated on a ACQUITY UPLC BEH C18 column (Waters™ 1.7 µm particle size, 2.1×50 mm) with a mobile phase consisting of a mixture of 0.1% formic acid in water (solvent A) and 0.1% formic acid in acetonitrile (solvent B). Gradient programming was used with a flow rate of 600 µl/min. After equilibration with 95% solvent A, 5 µl of sample was injected. Following a latency period of 0.25 min, the sample was eluted with a linear gradient of 5-100% solvent B over a period of 0.65 minutes followed by a 0.35 minutes hold. The column was prepared for the next sample by re-equilibrating over 0.25 minutes to the starting conditions. The column eluent was directly introduced into the ion source of the triple quadrupole mass spectrometer TQD™ (Waters Corporation, Milford, Mass., USA) controlled by Masslynx™ 4.1 software. Electrospray positive ionization (ESI+) multiple reaction monitoring was used for the MS/MS detection of the analyte. Precursor to product ion transitions of m/z 555.3-□ m/z 329.2 for compound A were used. The limit of quantification (LOQ) for the compound was set to 0.7 ng/mL (CV and overall bias less than 30%). Regression analysis and further calculations were performed using QuanLynx™ 4.1 (Micromass) and Excel™ 2007 (Microsoft). Concentrations of unknown samples were back-calculated based on the peak area ratios of analyte/IS from a calibration curve constructed using calibration samples spiked in blank plasma or tissue obtained from animals treated with vehicle.

Calculation of the Pharmacokinetic Parameters

Areas under the plasma concentration versus time curves (AUC) were calculated from the mean values with linear trapezoidal rule, and further relevant parameters by using a non-compartmental model for extravascular dosing (Win-Nonlin® Professional Version 5.2, Pharsight corp., CA, US).

Immuno-Histochemistry

All tissues were processed to FFPE according to routine procedures and following fixation, rat sternum was decalcified in Citrate/EDTA buffer for 5 days, with buffer exchange every 24 h. Sections were cut at 3 µm using a microtome. p21 and cleaved Caspase-3 immunohistochemistry was performed on a Ventana Discovery XT automated immunostainer using the OmniMap anti Mouse or Rabbit HRP secondary reagent and the ChromoMap DAB chromogen system (Ventana/Roche Diagnostics GmbH, Mannheim, Germany). Antigen retrieval was done by using Cell Conditioning Discovery CC1 (Ventana/Roche Diagnostics) at mild (95° 8 min+100° 20 min, for cleaved Caspase-3) or standard (95° 8 min+100° 36 min, for p21) conditions. The primary antibody was applied manually at the desired dilution in Dako antibody diluent, followed by incubation for 1 hour at room temperature. Corresponding negative controls were incubated with AbD only. Counterstaining of sections was done using hematoxylin (Ventana/Roche Diagnostics). After the automated staining run, slides were dehydrated in a graded series of ethanol, cleared in xylene and mounted with Pertex mounting medium.

Primary antibodies used for immunohistochemistry are described in Table 2.

TABLE 2

Antibodies used for immunohistochemistry

| Antibodies | Species | Clone | References | Dilution range |
|---|---|---|---|---|
| Mdm2 | Mouse mAb | SMP14 | SC, cat. 965 | 1/200 |
| p21 | Mouse mAb | SX118 | Dako, cat. M7202 | 1/50 |
| p21 | Mouse mAb | F-5 | SC, cat. 6246 | 1/50 |
| Cleaved Caspase-3 | Rabbit polyclonal Ab | — | CST, cat. 9661 (Lot #37) | 1/2000 |
| Cleaved Caspase-3 | Rabbit mAb | 5A1E | CST, cat. 9664 | 1/200 |

This table shows the source of the antibodies used for immunohistochemistry, as well as their dilution.

mRNA In Situ Hybridization

In situ hybridization was performed using the QuantiGene ViewRNA FFPE Assay kit (Affymetrix/Panomics) following the manufacturer's protocol. Gene-specific probe sets for rat Ubc (Ubiquitin C) and Bbc3 (PUMA) mRNAs were custom-designed and synthesized by Affymetrix. Bbc3 probes were used in type 1/Fast Red and Ubc probes were used in type 6/Fast Blue. Slides were processed strictly following the QuantiGene protocol. Pre-hybridization conditions were found to be optimal with 10 min of boiling in pre-treatment solution (Affymetrix) and 10 min of Protease QF (Affymetrix) digestion at 40° C. Briefly, five micrometer sections were cut, fixed in 10% formaldehyde, deparaffinized and rehydrated. In order to increase accessibility to mRNAs, slides were then boiled in pre-treatment solution (Affymetrix) and digested with protease QF (Affymetrix) at optimal conditions. Sections were then hybridized for 3 h at 40° C. with custom-designed QuantiGene ViewRNA probes against Bbc3 and the control gene Ubc. A no-probe sample was utilized as a negative control per the Affymetrix manual's recommendations. After hybridization, unbound probes were then flushed out with wash Buffer (Affymetrix) whereas bound probes were then amplified per protocol from Affymetrix (branched DNA amplification) using Pre-Amp (25 mn at 40° C.), then Amp molecules (15 mn at 40° C.) and finally multiple Label Probe oligonucleotides conjugated to alkaline phosphatase (LP-AP) for 15 mn at 40° C. LP-AP type 6 probe detection of signal was done with Fast Blue substrate (blue dots, Cy5 fluorescence) for 30 mn at RT in the dark, followed by LP-AP type 1 probe detection of signal with Fast Red Substrate (red dots, Cy3 fluorescence) for 30 mn at 40° C. After signal detection, slides were then counterstained with Mayer's haematoxylin, rinsed and mounted/coversliped by using Ultramount aqueous mounting medium (DAKO). Images were taken with an Olympus BX51 microscope equipped with a ColorViewlll color camera (Soft Imaging Sytem).

Probes used for mRNA ISH are described in Table 3.

TABLE 3

Probes used for mRNA ISH

| Probes | References |
| --- | --- |
| Rat Ubc (Ubiquitin C) | Affimetrix, cat. VC6-10047-1 |
| Rat Bbc3 (PUMA) | Affimetrix, cat. VC1-13801-1 |

Example 1

Pharmacokinetics (PK) of Compound a after Single i.v. Injection at 20 mg/kg

Figure 2:
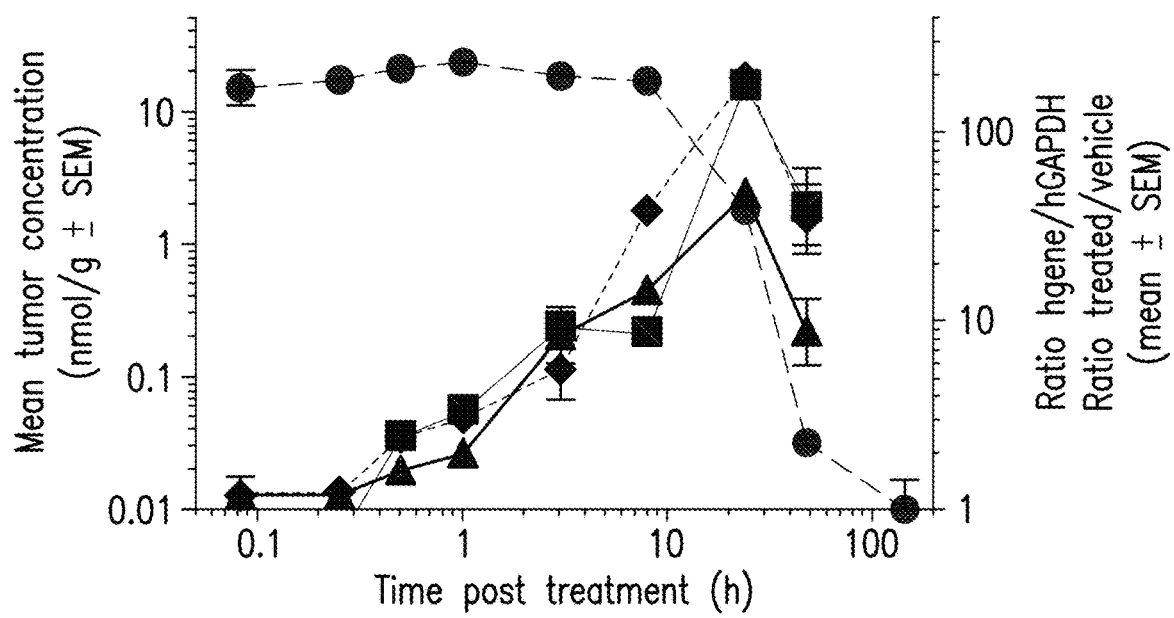
FIG. 2 depicts the PK and PD of Compound A on SJSA-1 tumor-bearing rat after one single i.v. treatment

FIG. 1 shows Compound A concentration in plasma, tumor and liver over 144 hours after one single i.v. injection. The Tmax for the compound was 5 min in plasma and liver and 1 h in tumor. Compound A had a two times higher exposure in tumor ($AUC_{0-144\,h}$ dn=16.5 h·nmol/g) compared to plasma ($AUC_{0-144\,h}$ dn=8.1 h·µM). FIG. 2 shows the Compound A concentration in tumor and the pharmacodynamics (PD) response in tumor. Puma and p21 had a very similar mRNA induction reaching an expression max of 180 and 200-fold 24 h post treatment, respectively.

Example 2

Figure 3:
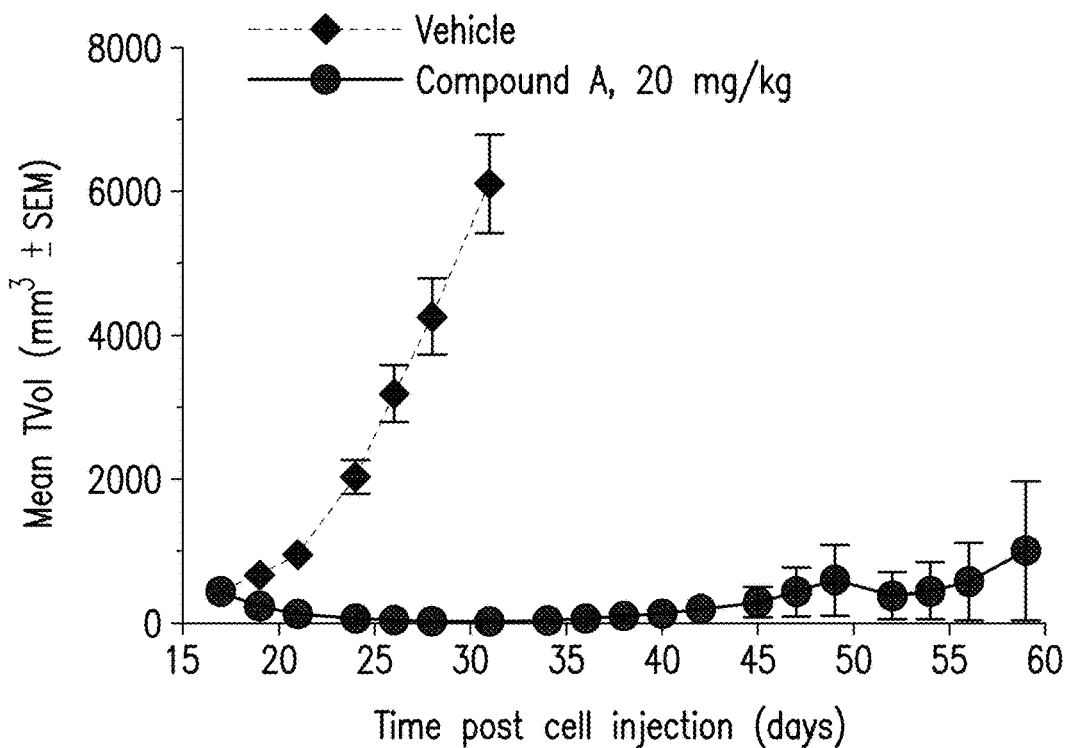
FIG. 3 depicts the Tumor growth after a single i.v. treatment of SJSA-1 tumor-bearing nude rat with compound A
Figure 4:
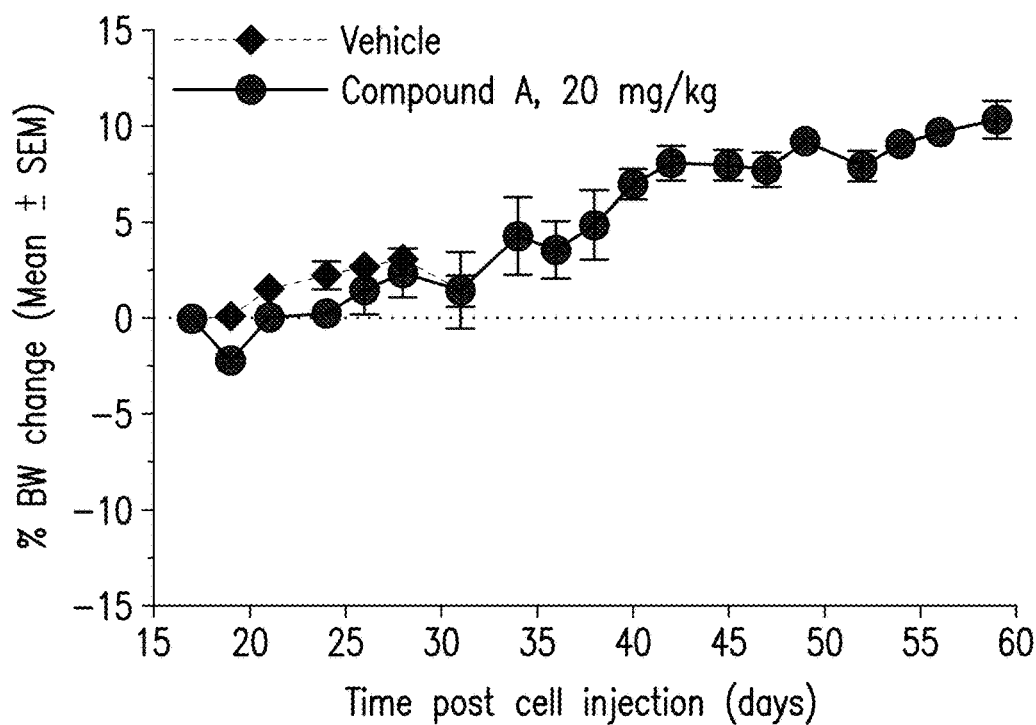
FIG. 4 depicts the Change in body weight (BW) after a single i.v. treatment of SJSA-1 tumor-bearing nude rat with compound A
Figure 5:
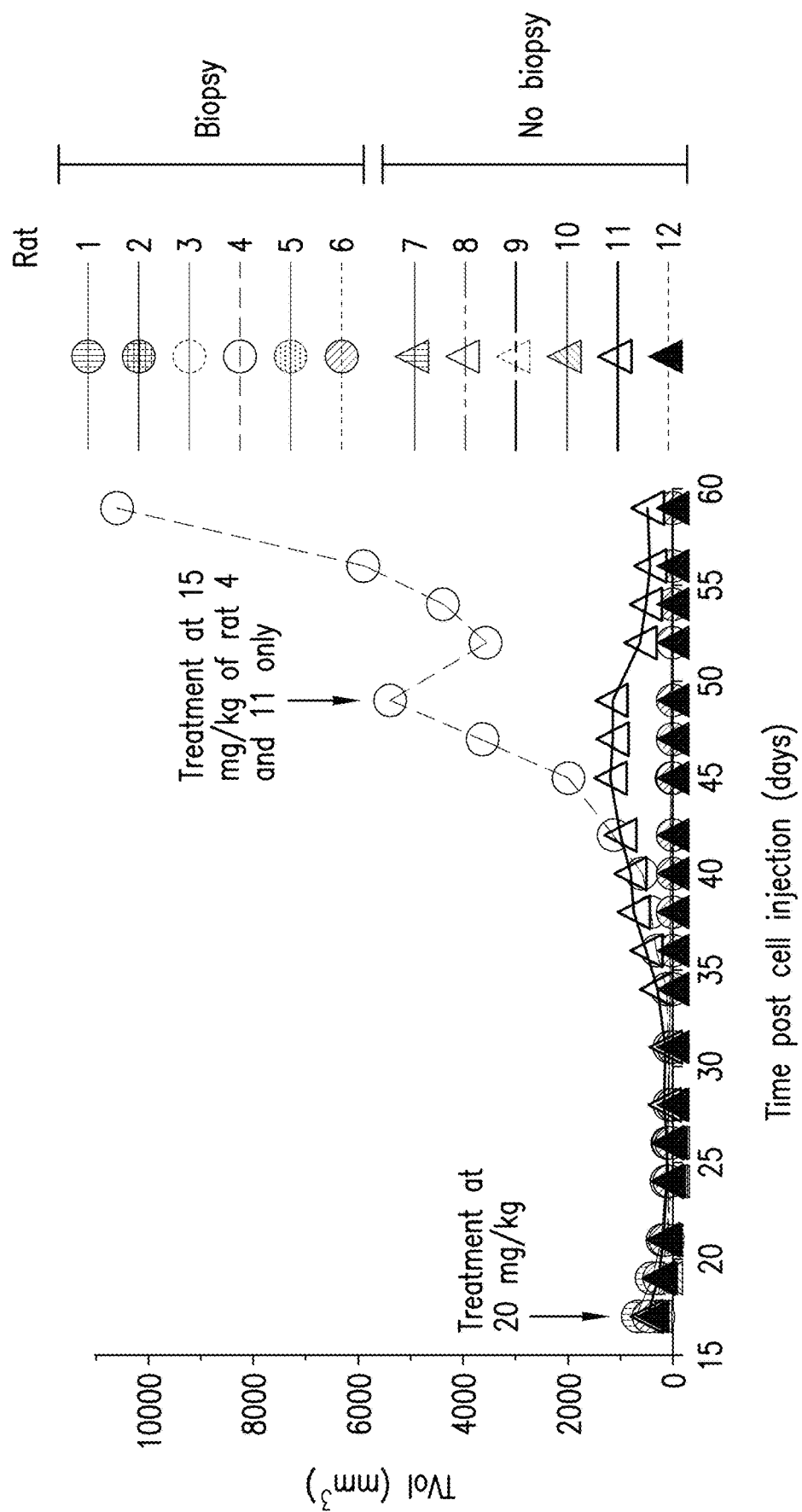
FIG. 5 depicts the Efficacy of compound A after a single i.v. treatment of SJSA-1 tumor-bearing nude rat—individual data
Figure 6:
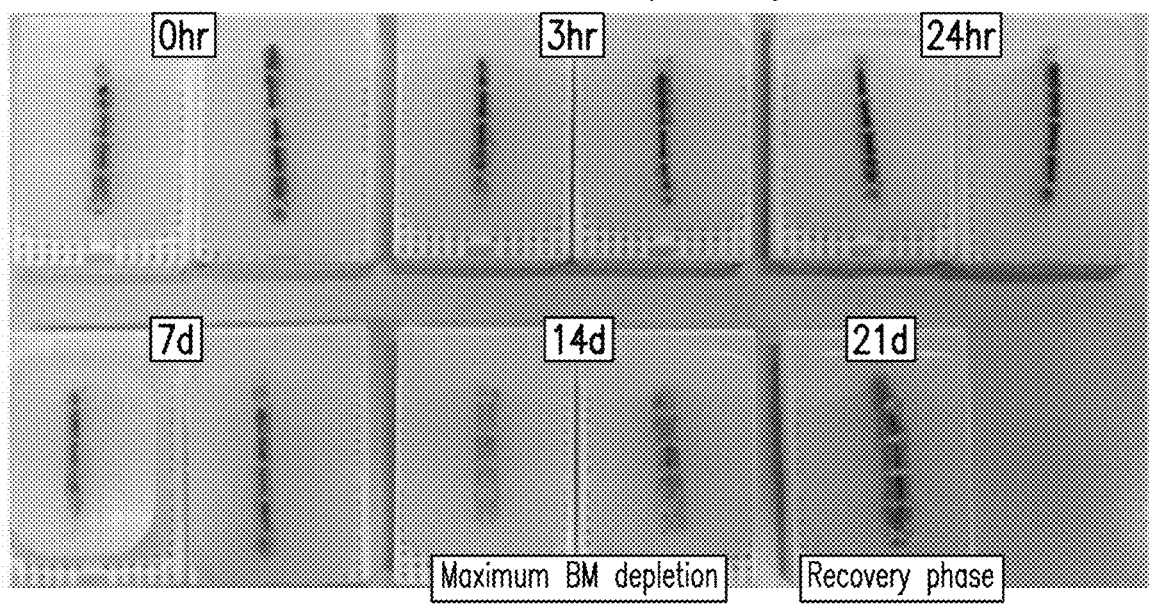
FIG. 6 depicts the Bone marrow recovery after a single i.v. treatment
Figure 6:
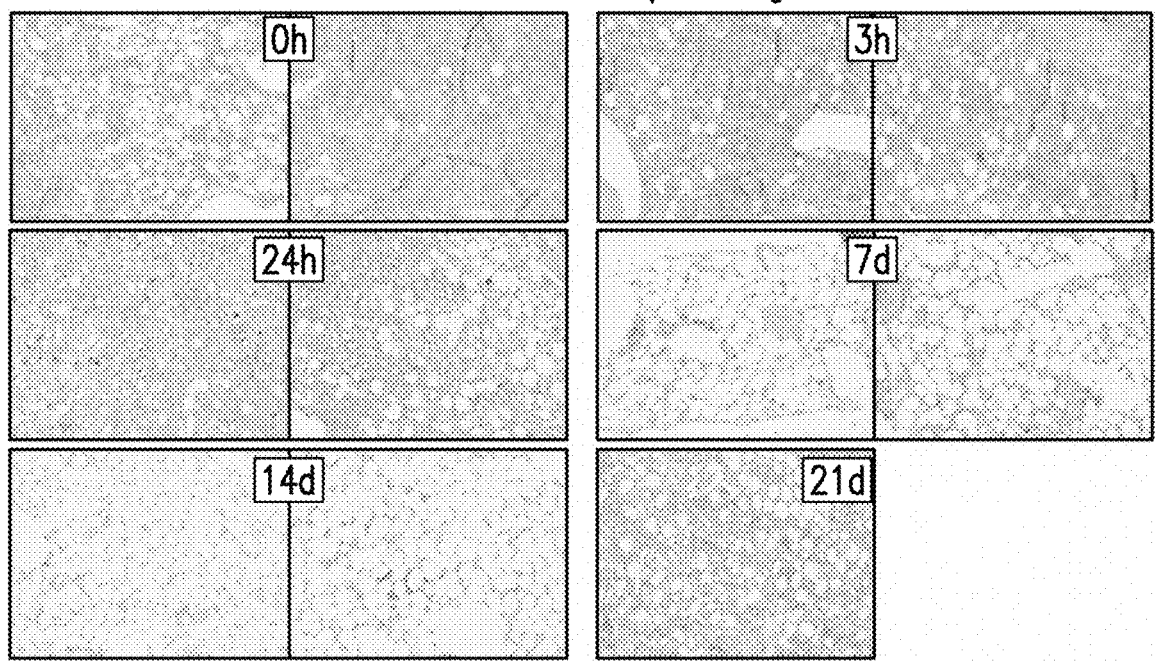
Figure 7:
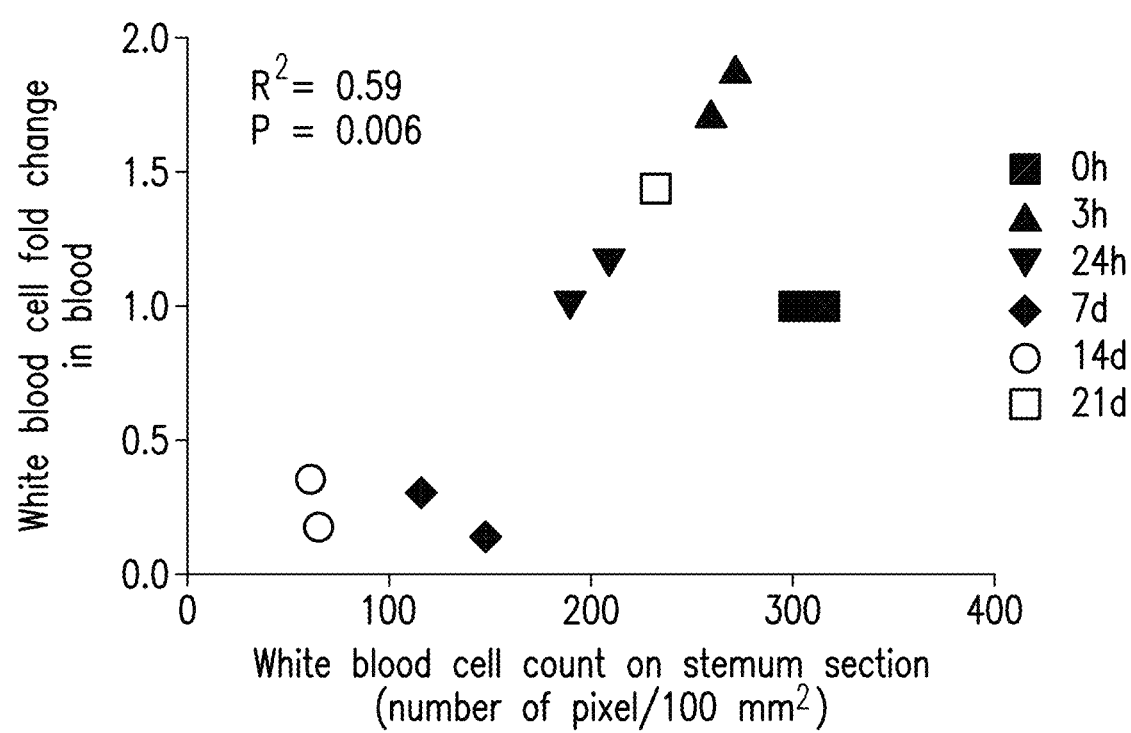
FIG. 7 depicts the Correlation between white blood cell count in blood and on bone marrow section from sternum

PK, PD, Efficacy and Tolerability of Compound A (i.v., Once) on SJSA-1 Tumor-Bearing Rat FIG. 3 and FIG. 4, respectively show the tumor growth and the change in body weight of nude rats over 42 days. The single i.v. treatment with compound A at 20 mg/kg (the higher dose) induced 92% tumor regression 14 days post treatment. One rat had to be sacrificed on day 9 post treatment because of excessive body weight (BW) loss. In spite of a slight decrease in BW 3 days post treatment for all others rats, they recovered quickly and gained BW during the entire experiment. Only 2 of 11 tumors had an incomplete response and regrew (FIG. 5). These 2 animals were retreated i.v. at 15 mg/kg and the tumors were still sensitive. However, tumor regression was attenuated which could be due to the larger tumor size. After the first treatment, p21 and Puma mRNA expression in tumor reached a more than 50-fold increase in mRNA expression. Mdm2 had a much lower mRNA induction (Emax=10-fold). On day 59 post first treatment, all rats were treated i.v. at 20 mg/kg in order to assess the effect of the drug on the host. The exposure of compound A was similar in heart, jejunum, spleen, liver and bone marrow but twice as high as in plasma (Cmax not known). The maximum increase in p21, Mdm2 and cleaved Caspase-3 in jejunum and bone marrow (sternum) was always observed 3 h post treatment. All staining were back to baseline 7 days post treatment. The increase in cleaved caspase-3 on jejunum section showed a strong correlation with the Puma (Bbc3) mRNA induction detected by mRNA ISH. Indeed, the maximum increase in Puma was observed 3 h post last treatment with a return to baseline 7 days post treatment. RNA ISH clearly showed that only crypt cells were stained on jejunum section. The same was true in spleen and heart. Finally, severe bone marrow depletion could be observed 14 days post treatment with partial recovery on day 22 (FIG. 6). The white blood cell count showed that it significantly correlated with the bone marrow depletion ($R^2$=0.59, P=0.006, FIG. 7). This indicates the intermittent dosing can improve tolerability due to allowing bone marrow to recover.

Example 3

Figure 8A:
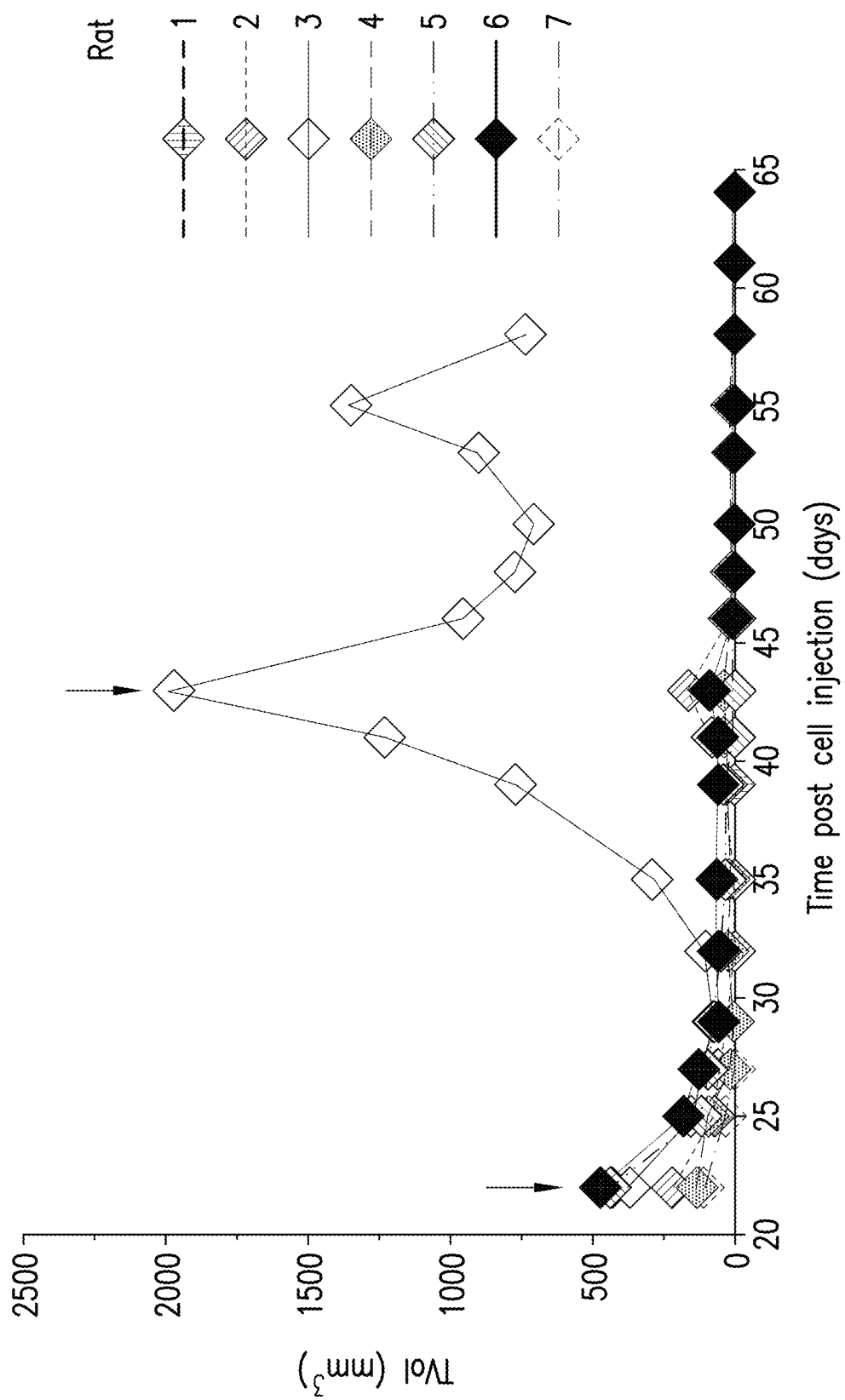
FIG. 8A shows the tumor growth and the change in body weight of nude rats over 42 days after i.v. (q3w, i.e. once every three weeks) treatment of SJSA-1 tumor-bearing nude rat.
Figure 8B:
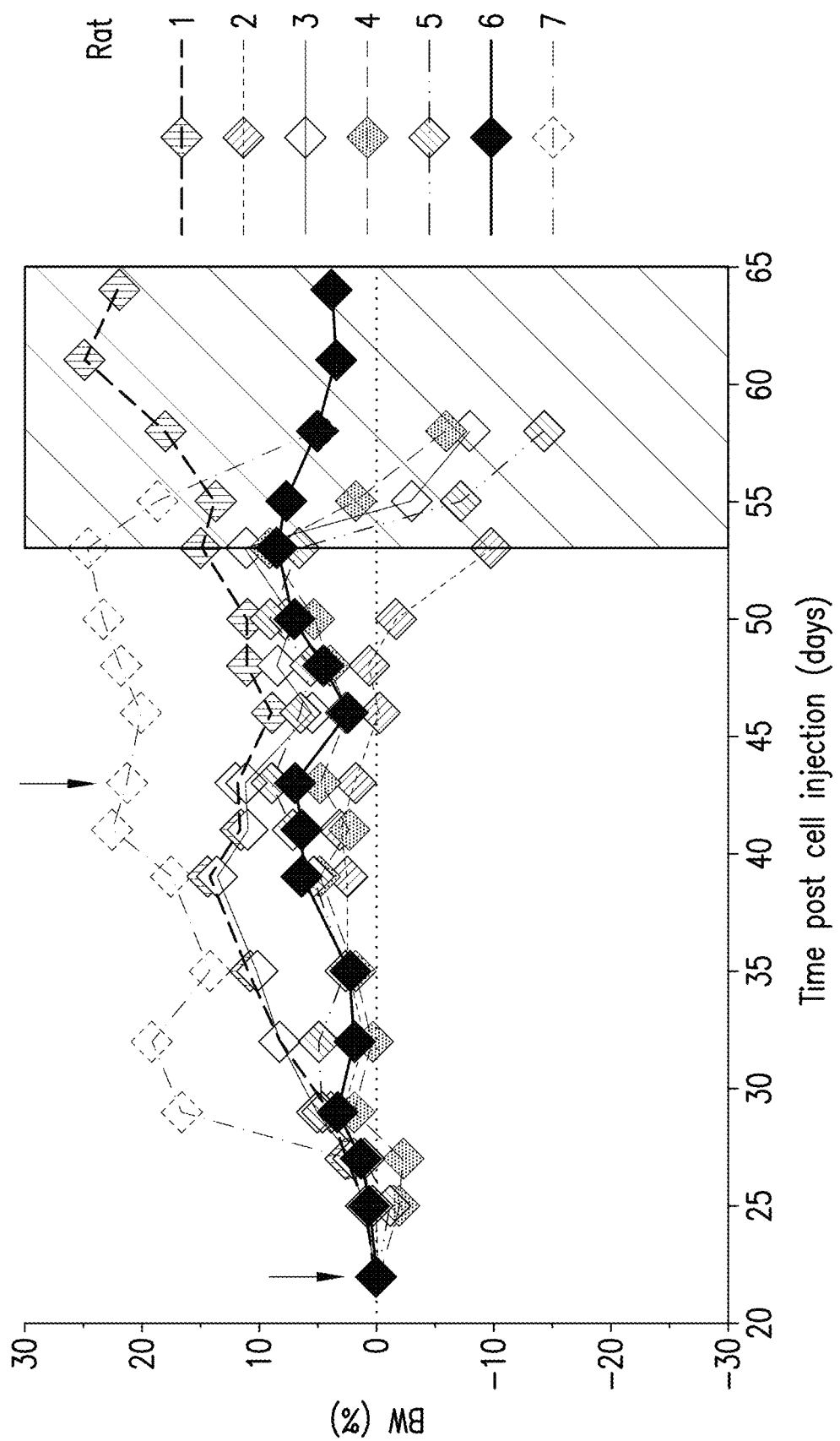
FIG. 8B shows the tumor growth and the change in body weight of nude rats over 42 days after i.v. (q3w, i.e. once every three weeks) treatment of SJSA-1 tumor-bearing nude rat.
Figure 9A:
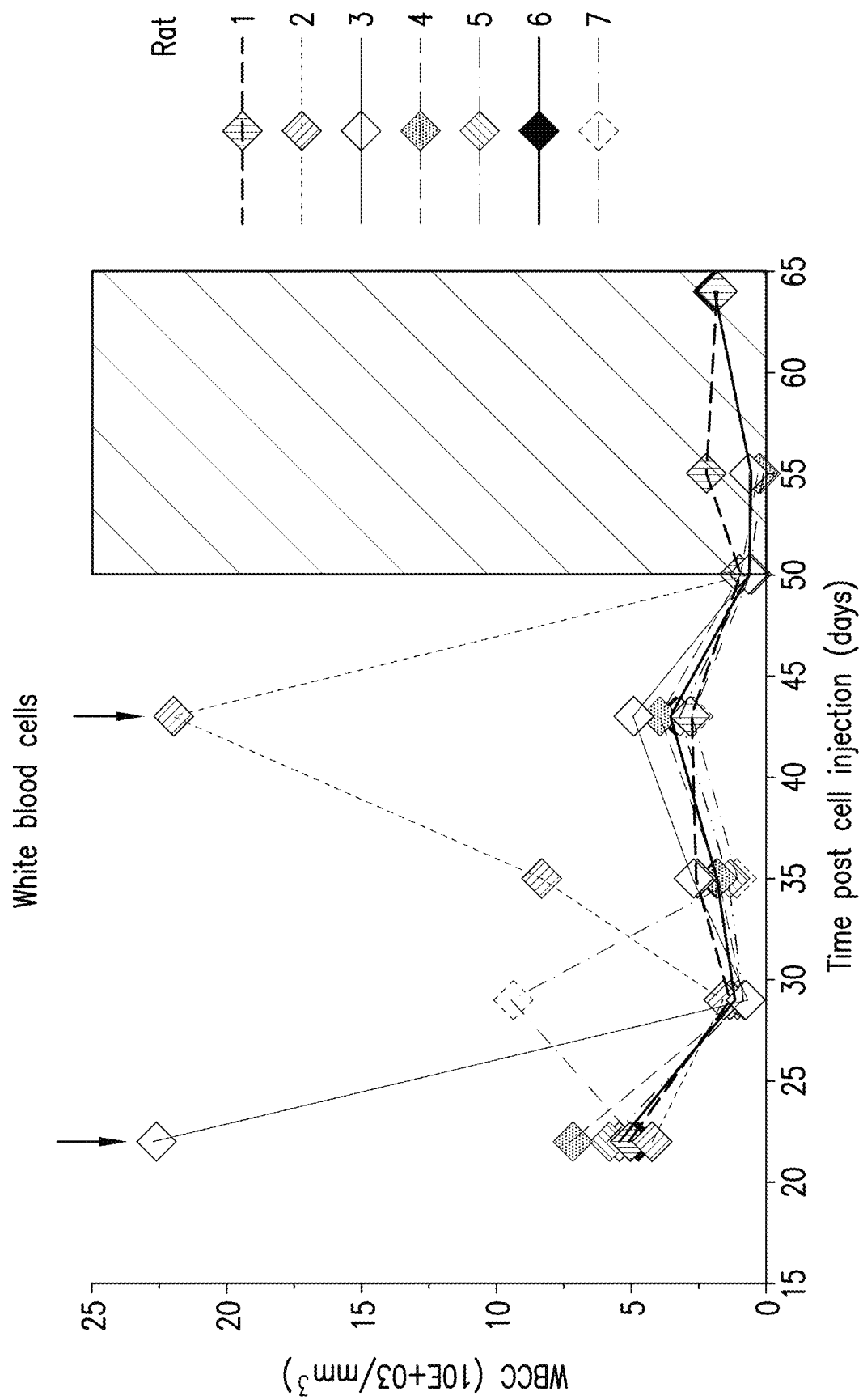
FIG. 9A depicts the Effect of the i.v. treatment (q3w) on the white blood cells (WBC)
Figure 9B:
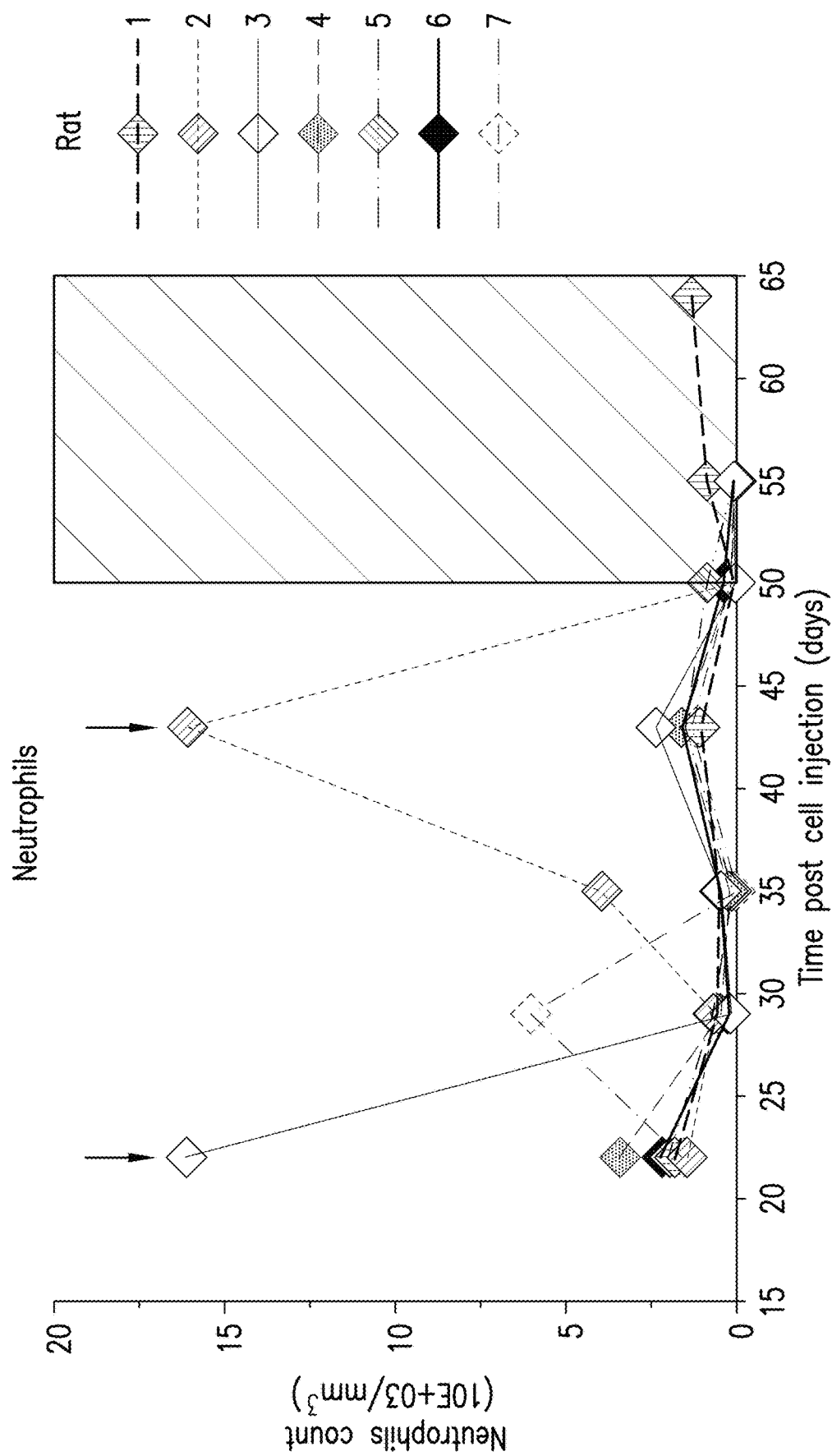
FIG. 9B depicts the Effect of the i.v. treatment (q3w) on neutrophils
Figure 9C:
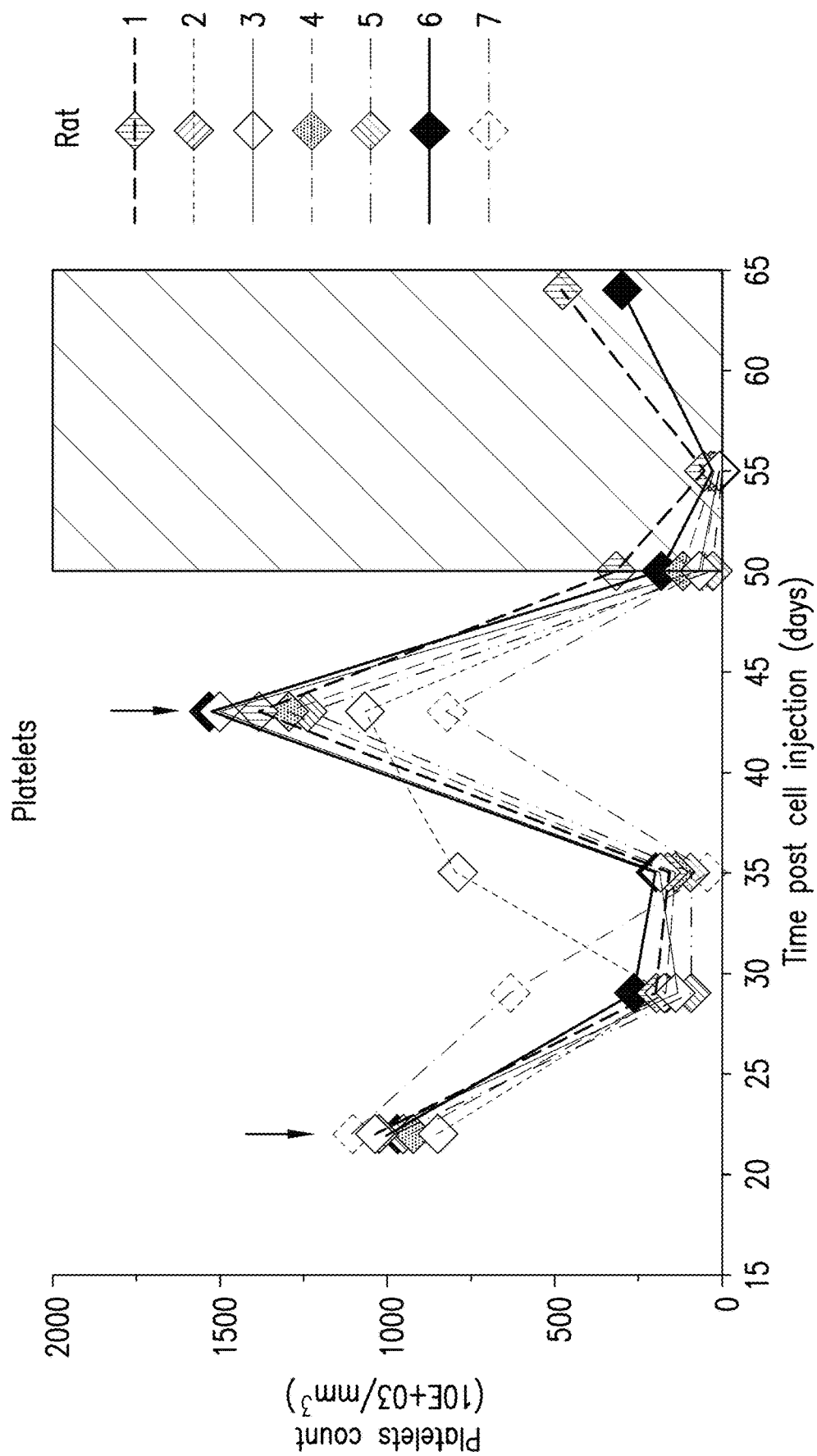
FIG. 9C depicts the Effect of the i.v. treatment (q3w) on the platelet count

PK, PD, Efficacy and Tolerability of Compound A (i.v., q3w) on SJSA-1 Tumor-Bearing Rat FIG. 8A and FIG. 8B shows the tumor growth and the change in body weight of nude rats over 42 days. Three weeks post first treatment at 20 mg/kg, compound A induced 6% tumor regression on average. However, individual data show that 3 rats had complete response (100% regression), 2 had partial response (more than 50% regression), 1 had stable disease and 1 had progressive disease in spite of an early 80% regression 1 week post treatment. After the second treatment, Compound A induced 100% tumor regression but only 2/7 animals survived the 2 full cycles. Indeed, 5 rats had to be sacrificed after the second treatment because of excessive BW loss: the first one 10 days post second treatment and the four others 8 days later. FIG. 9A, FIG. 9B and FIG. 9C shows the white blood cells (WBC), neutrophils and platelets count over the 42 days of experiment. Compound A induced a dramatic decrease in WBCs, neutrophils and platelets after the first treatment and most rats only partially recovered on day 21 post treatment. As a consequence, the second treatment brought the WBCs, neutrophils and platelets to an extremely low level close to 0.

Example 4

Figure 10A:
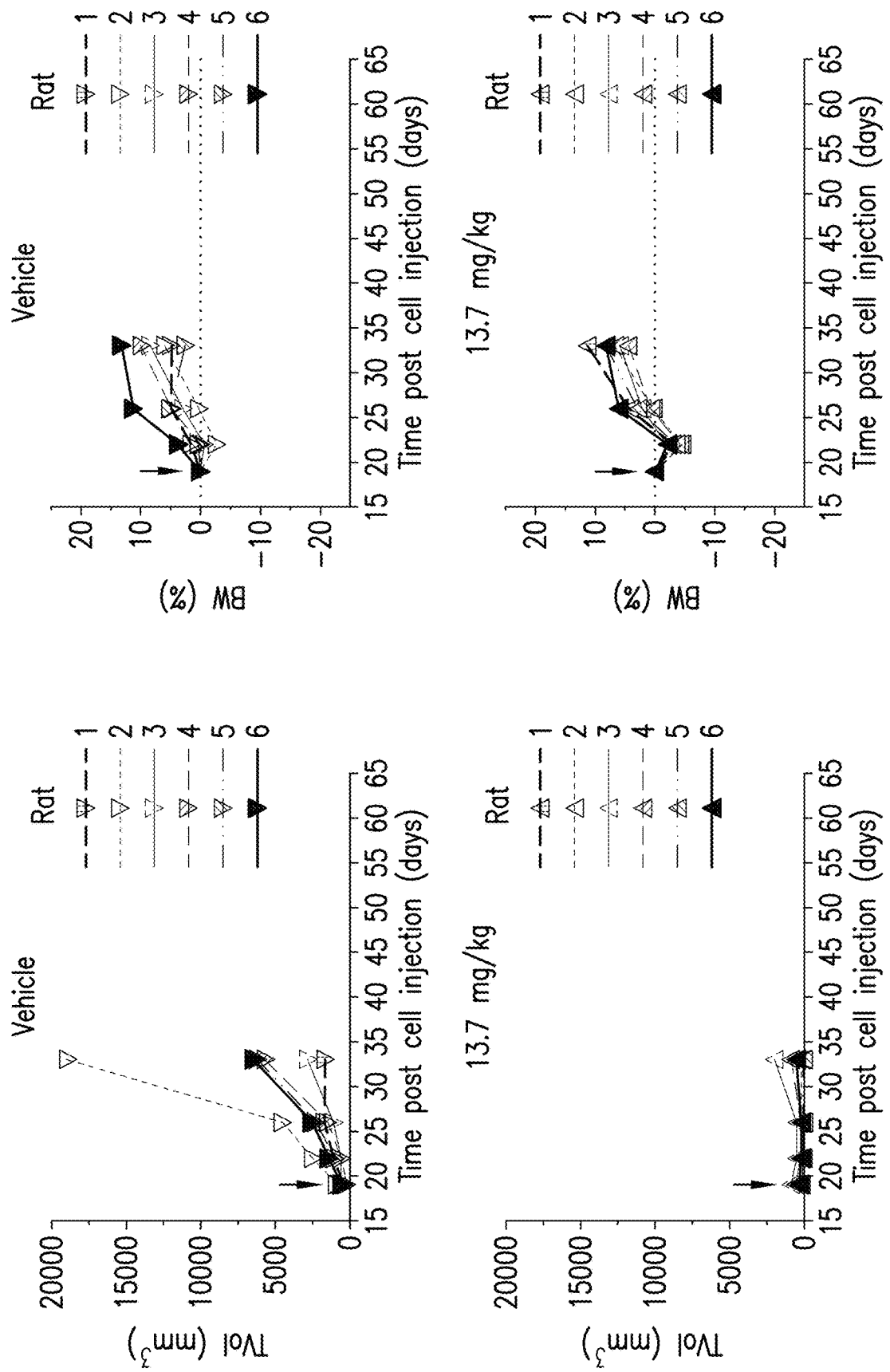
FIG. 10A shows the tumor growth and the change in body weight of nude rats over 42 days of q3w i.v. treatment with Compound A at 13.7 and 18.2 mg/kg
Figure 10B:
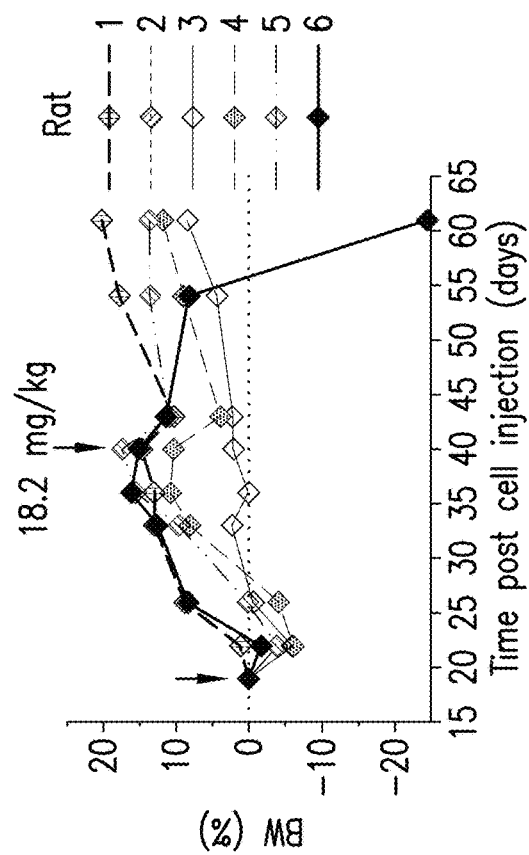
FIG. 10B shows the tumor growth and the change in body weight of nude rats over 42 days of q3w i.v. treatment with Compound A at 13.7 and 18.2 mg/kg
Figure 10B:
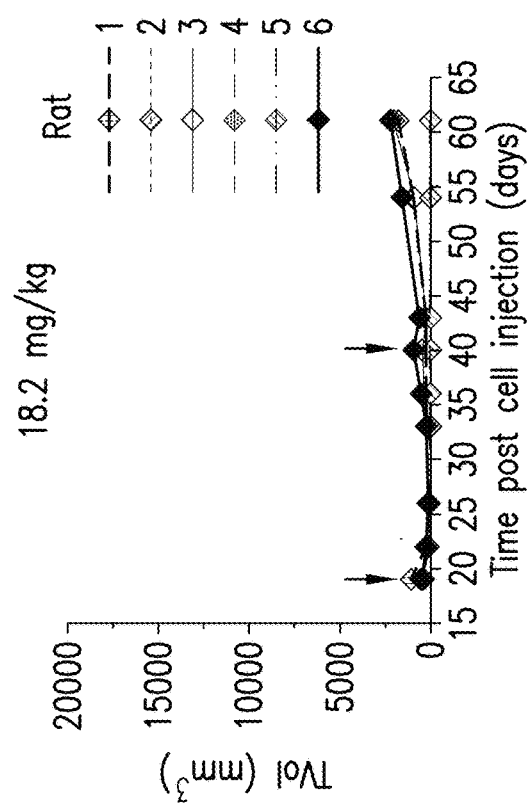
Figure 11A:
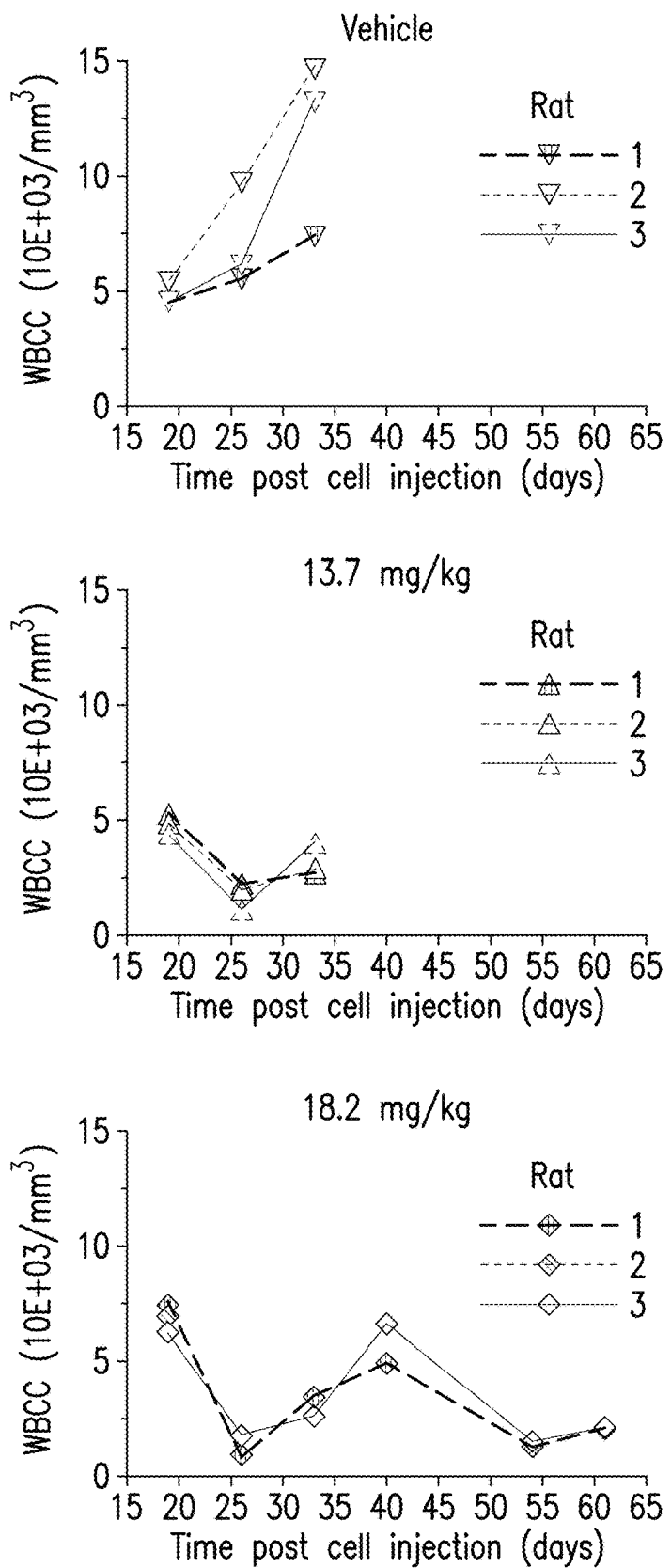
FIG. 11A depicts the Effect of the i.v. treatment (q3w) with Compound A at 13.7 and 18.2 mg/kg on the white blood cells (WBC)
Figure 11B:
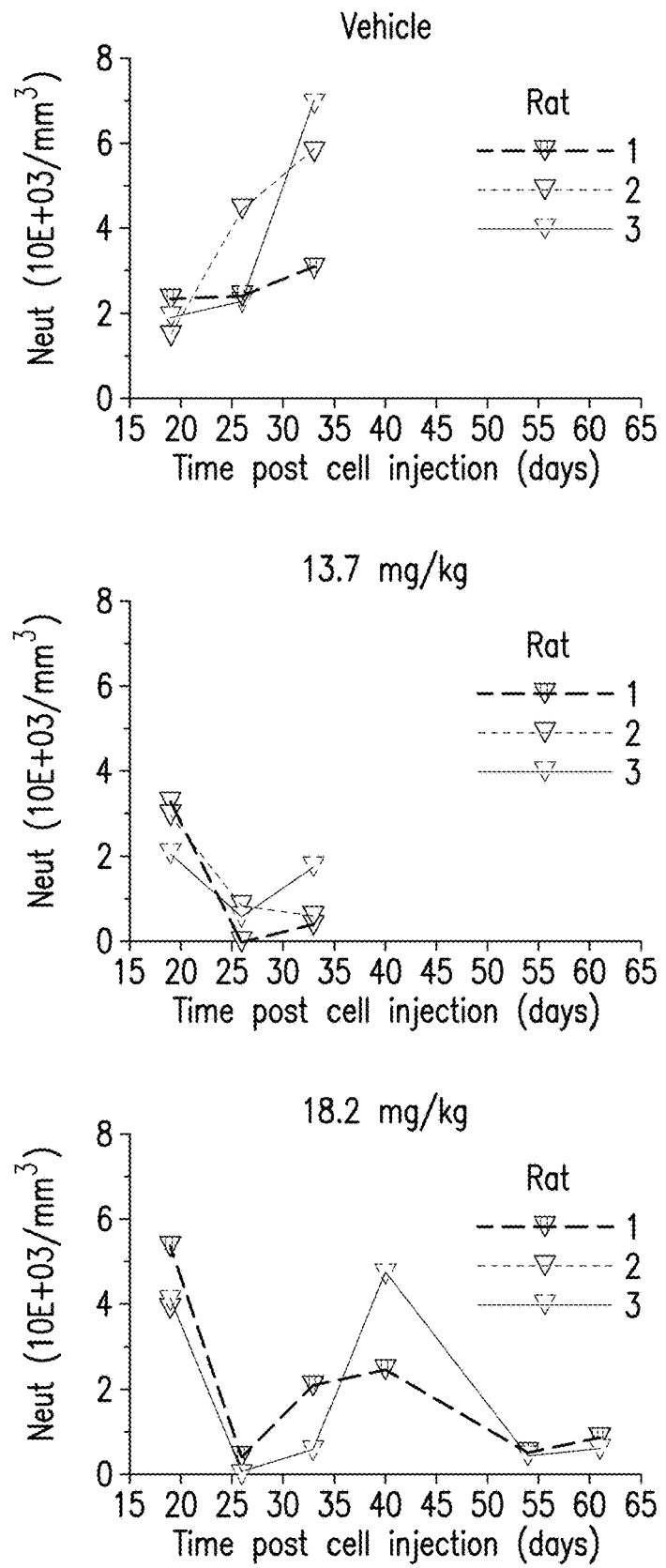
FIG. 11B depicts the Effect of the i.v. treatment (q3w) with Compound A at 13.7 and 18.2 mg/kg on the neutrophils
Figure 11C:
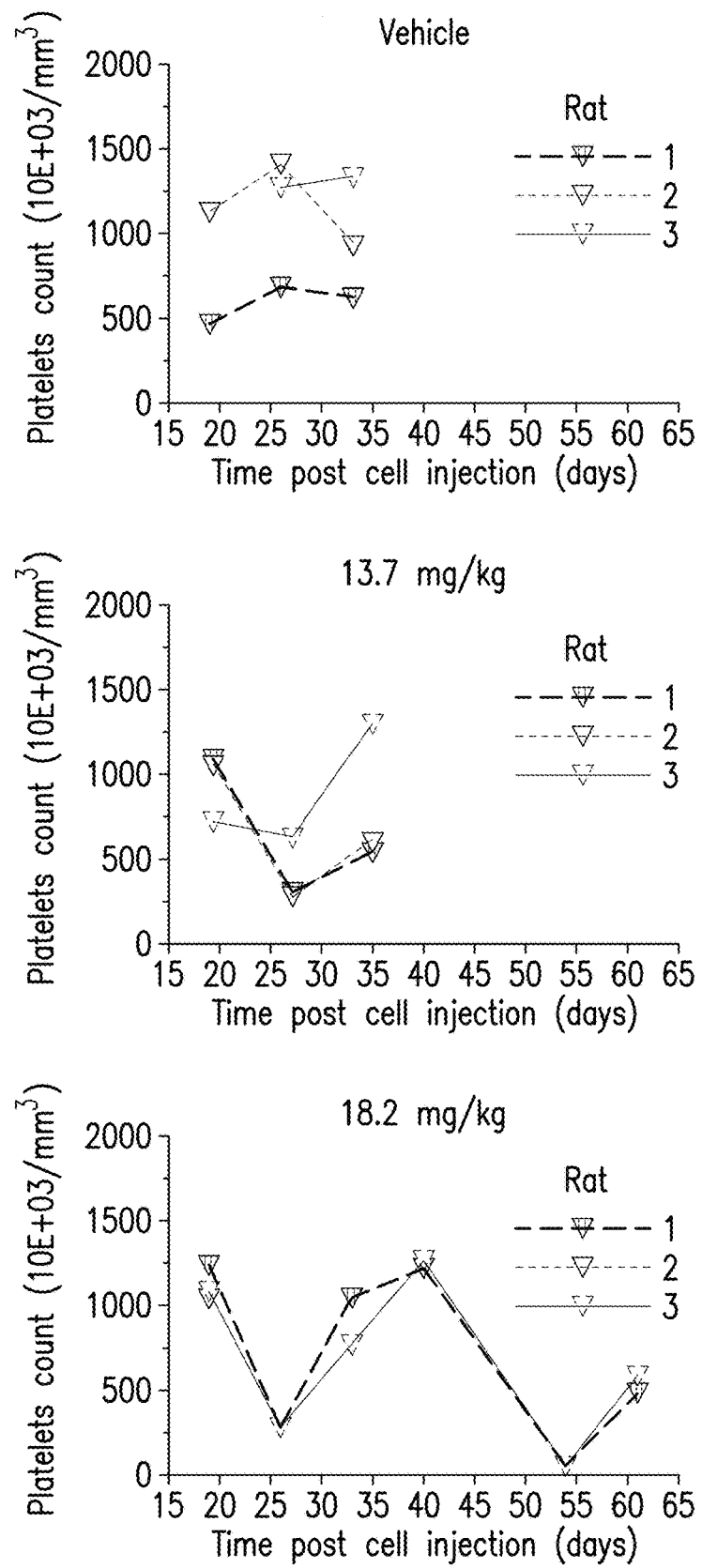
FIG. 11C depicts the Effect of the i.v. treatment (q3w) with Compound A at 13.7 and 18.2 mg/kg on the platelet count

PK, PD, Efficacy and Tolerability of Compound A (i.v., q3w) on SJSA-1 Tumor-Bearing Rat FIG. 10A and FIG. 10B shows the tumor growth and the change in body weight of nude rats over 42 days. The treatment with Compound A at 13.7 and 18.2 mg/kg could induce a 66 and 88% tumor regression in average one week post treatment. After two weeks, all the tumors treated at 13.7 mg/kg were re-growing and we decided to stop this treatment group. Three weeks post treatment at 18.2 mg/kg, the tumors were still regressing by 36% with 2 complete responses. The effect on the tumor growth tended to be less after the second treatment as on average, the tumors were progressing by 118% (Table 4) and the two same tumors had complete responses. As a consequence, the second treatment did not increase the number of complete responses. In terms of tolerability, the rats had a slight loss in BW 3 days post treatment, but they recovered quickly and had gained BW by the following treatment. Actually, only one rat had a dramatic loss in BW during the last day of the experiment and it cannot be determined if it was treatment related. FIG. 11A, FIG. 11B and FIG. 11C_shows the white blood cells, neutrophils and platelets count over the 42 days of experiment. Compound A induced a strong decrease in WBCs, neutrophils and platelets after the first treatment but all measured rats fully recovered on day 21 post treatment. The second treatment had a similar effect on cells count but rats only partially recovered on day 21 post second treatment.

TABLE 4

Efficacy and tolerability of Compound A after i.v. treatment (q3w) of SJSA-1 tumor-bearing nude rat (SF480)

| Treatment | Tumor | | | | Host | | | |
|---|---|---|---|---|---|---|---|---|
| i.v., q3w | 13.7 mg/kg | | 18.2 mg/kg | | 13.7 mg/kg | | 18.2 mg/kg | |
| Week post treatment | ΔTvol (%) | CR | ΔTvol (%) | CR | ABW (%) | Survival | ABW (%) | Survival |
| 1 | −66 ± 9 | 1/6 | −80 ± 2 | 0/5 | 2.7 ± 0.9 | 6/6 | 2.5 ± 2.6 | 5/5 |
| 2 | 4 ± 37 | 0/6 | −79 ± 11 | 2/5 | 7.5 ± 1.0 | 6/6 | 9.1 ± 1.9 | 5/5 |
| 3 | — | — | −36 ± 37 | 2/5 | — | — | 11.9 ± 2.7 | 5/5 |
| 5 | — | — | 22 ± 63 | 2/5 | — | — | 10.6 ± 2.3 | 5/5 |
| 6 | — | — | 118 ± 104 | 2/5 | — | — | 5.9 ± 7.9 | 5/5 |

Example 5

PK and PD with Compound a on SJSA-1 Tumor Bearing Rat after Single Oral Administration (27 mg/kg)

Figure 12:
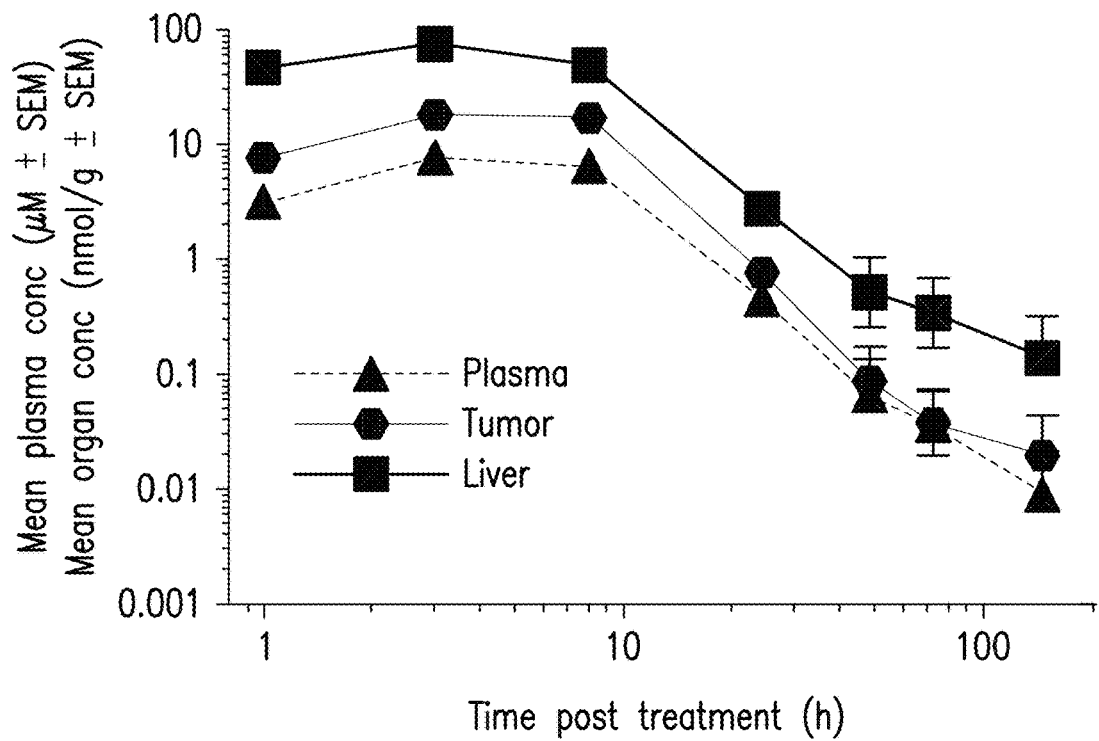
FIG. 12 depicts the PK study on SJSA-1 tumor bearing rat after one single treatment with compound A per os
Figure 13:
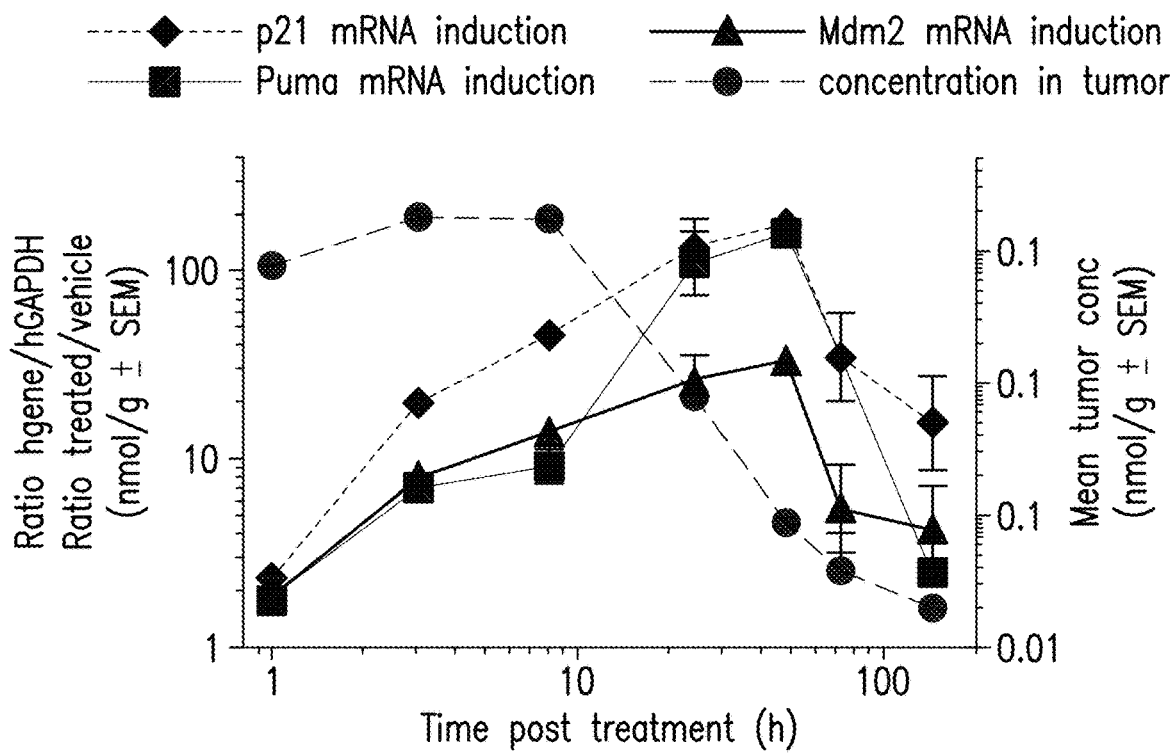
FIG. 13 shows the drug concentration and the PD response in tumor after single administration

FIG. 12 shows the drug concentration in plasma, tumor and liver over 144 hours after one single oral injection of Compound A. The Tmax for the compound was 3 hours (h) in all matrices. Compound A showed a higher exposure in tumor ($AUC_{0-144\ h}$=277.7 h·nmol/g) in comparison to plasma ($AUC_{0-144\ h}$=111.5 h·µM). FIG. 13 shows the drug concentration and the PD response in tumor. Puma and p21 had a similar mRNA induction reaching an Emax of 162 and 180-fold 48 h post treatment. At such p.o. dose, Mdm2 had a much lower Emax (34-fold).

Example 6

Efficacy on SJSA-1 Tumor Bearing Rat with a 3qw Dosing Regimen (p.o.)

Figure 14:
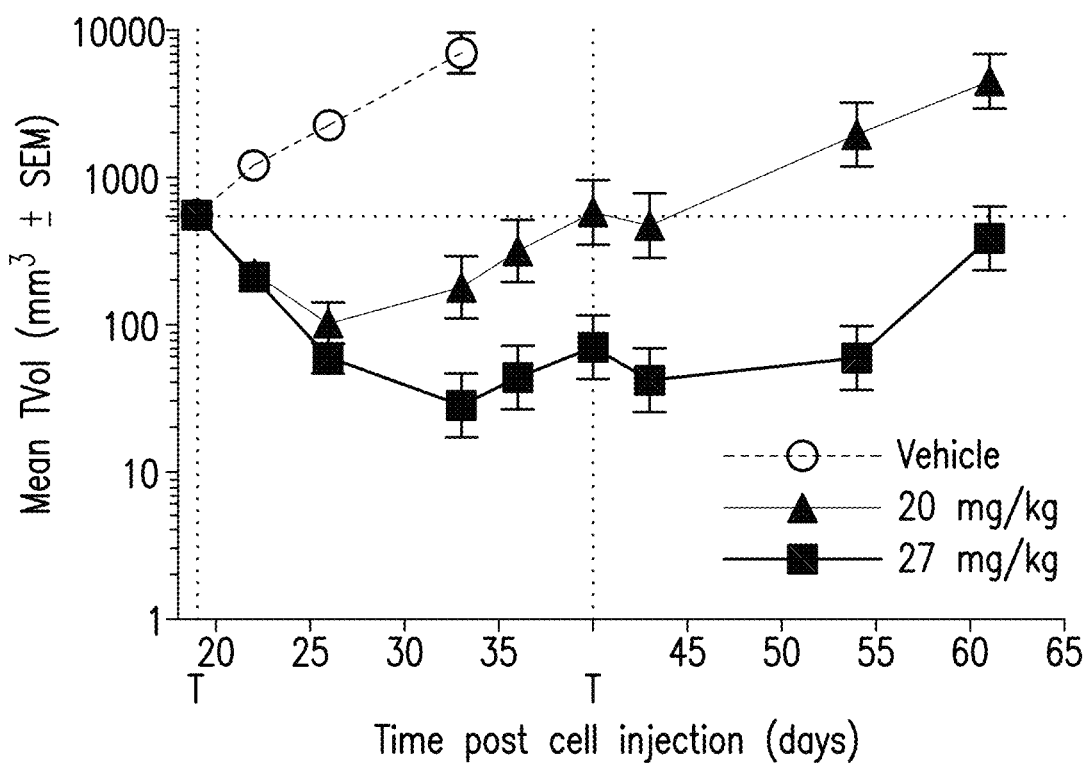
FIG. 14 shows the tumor growth and the change in body weight of nude rats over 42 days of q3w p.o. treatment with compound A
Figure 14:
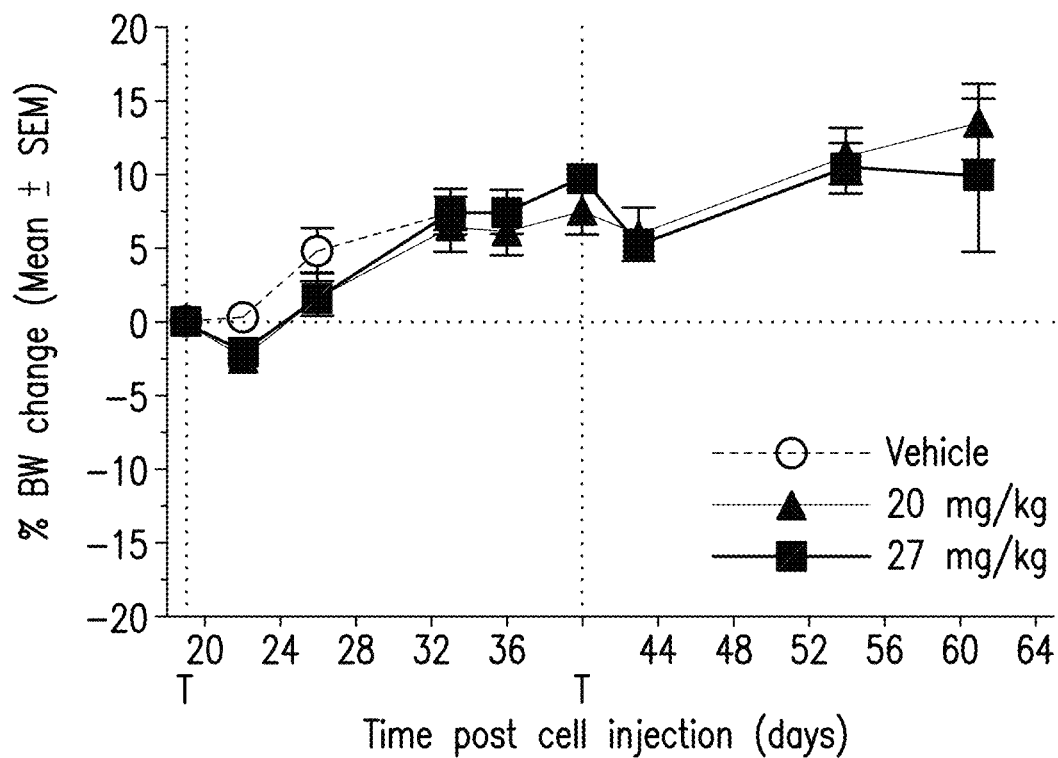
Figure 15A:
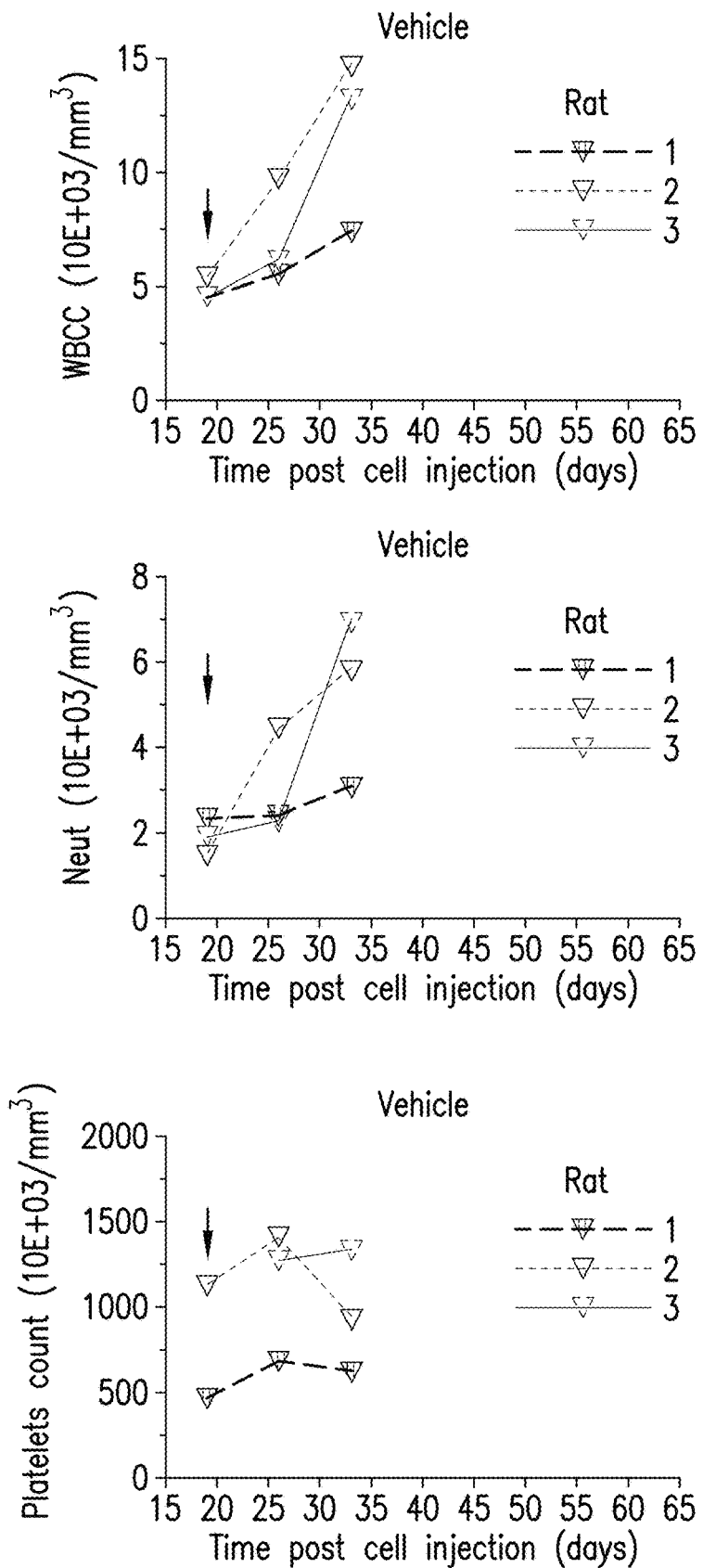
FIG. 15A shows the white blood cells and platelets count over the 42 days of q3w p.o. treatment with compound A
Figure 15B:
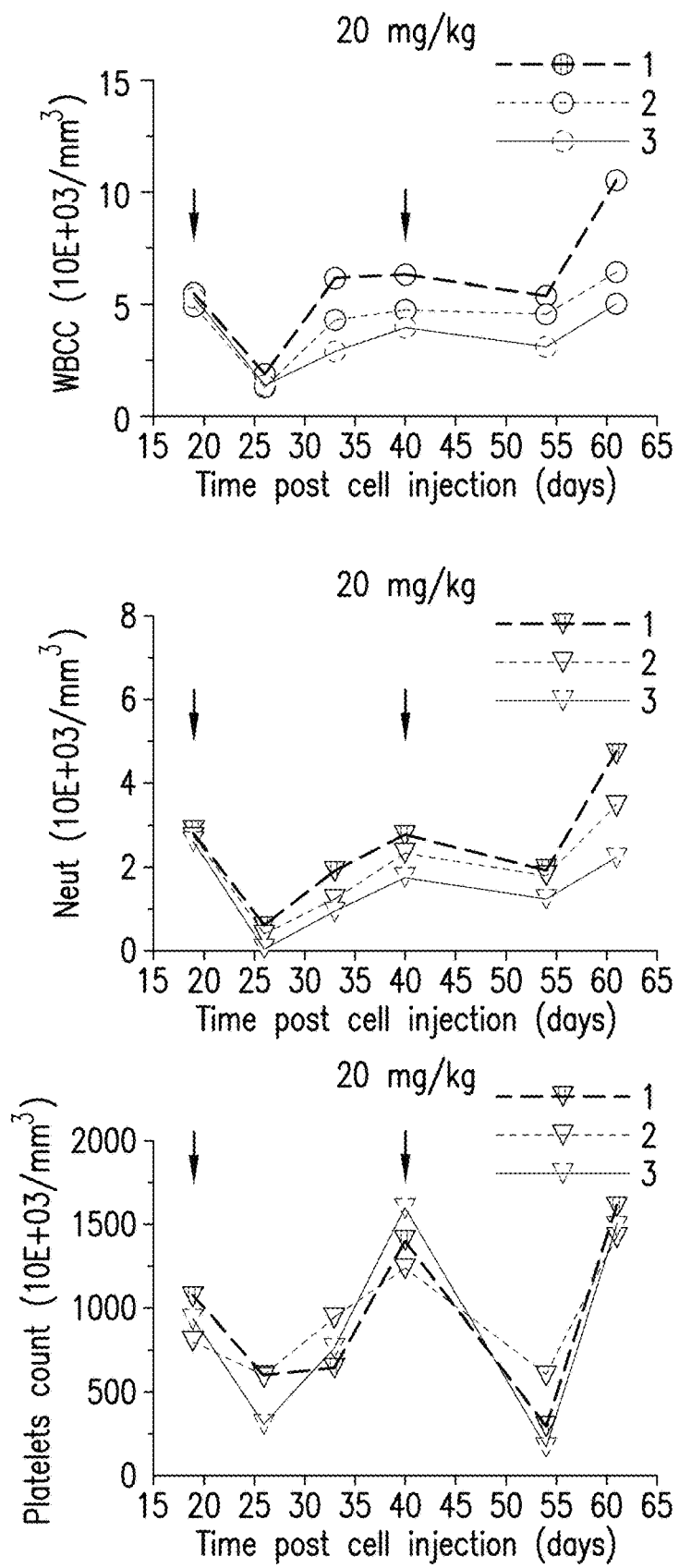
FIG. 15B shows the white blood cells and platelets count over the 42 days of q3w p.o. treatment with compound A
Figure 15C:
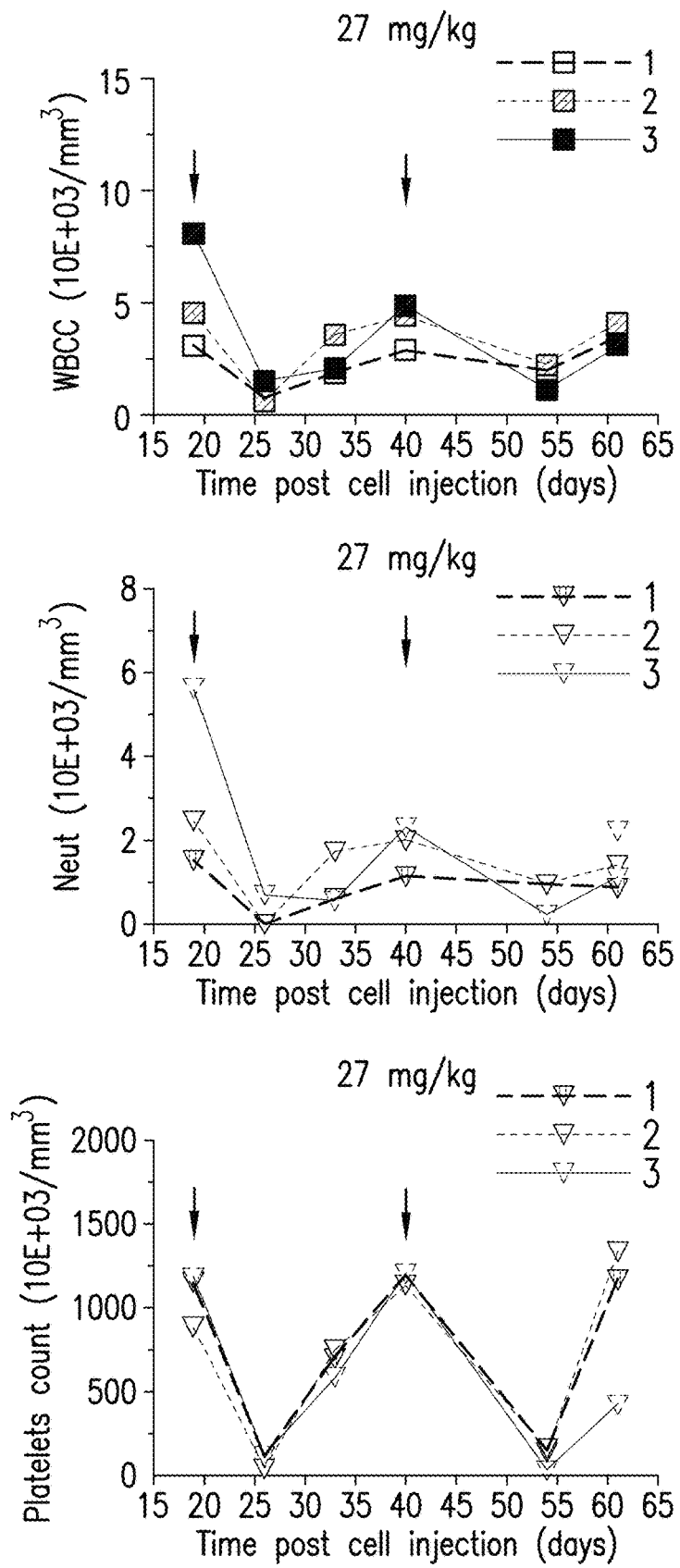
FIG. 15C shows the white blood cells and platelets count over the 42 days of q3w p.o. treatment with compound A

FIG. 14 shows the tumor growth and the change in body weight of nude rats over 42 days of q3w p.o. treatment with compound A. Three weeks post first treatment, both doses could induce a tumor regression (27 and 88% for the doses 20 and 27 mg/kg respectively). However the effect on the tumor growth tended to be mitigated after the second treatment as only the highest dose could still induce a tumor regression (27% at 27 mg/kg). After the first treatment, Cmax and $AUC_{0-24\ h}$ of compound A in blood and p21 and Puma mRNA expression in tumor nicely and dose-dependently increased. Both doses induced a slight decrease in bodyweight (BW) 3 days post each treatment but all animals recovered quickly and had a gain in BW 3 weeks post treatment. FIG. 15A, FIG. 15B and FIG. 15C_shows the white blood cells and platelets count over the 42 days of experiment. Compound A induced a dose-dependent decrease in WBCs, neutrophils and platelets. WBCs and platelets fully recovered before the second treatment at 20 mg/kg. For the treatment at 27 mg/kg, platelets also fully recovered but WBCs only partially.

Example 7

Effect of a Low Dose Versus High Dose

Figure 16:
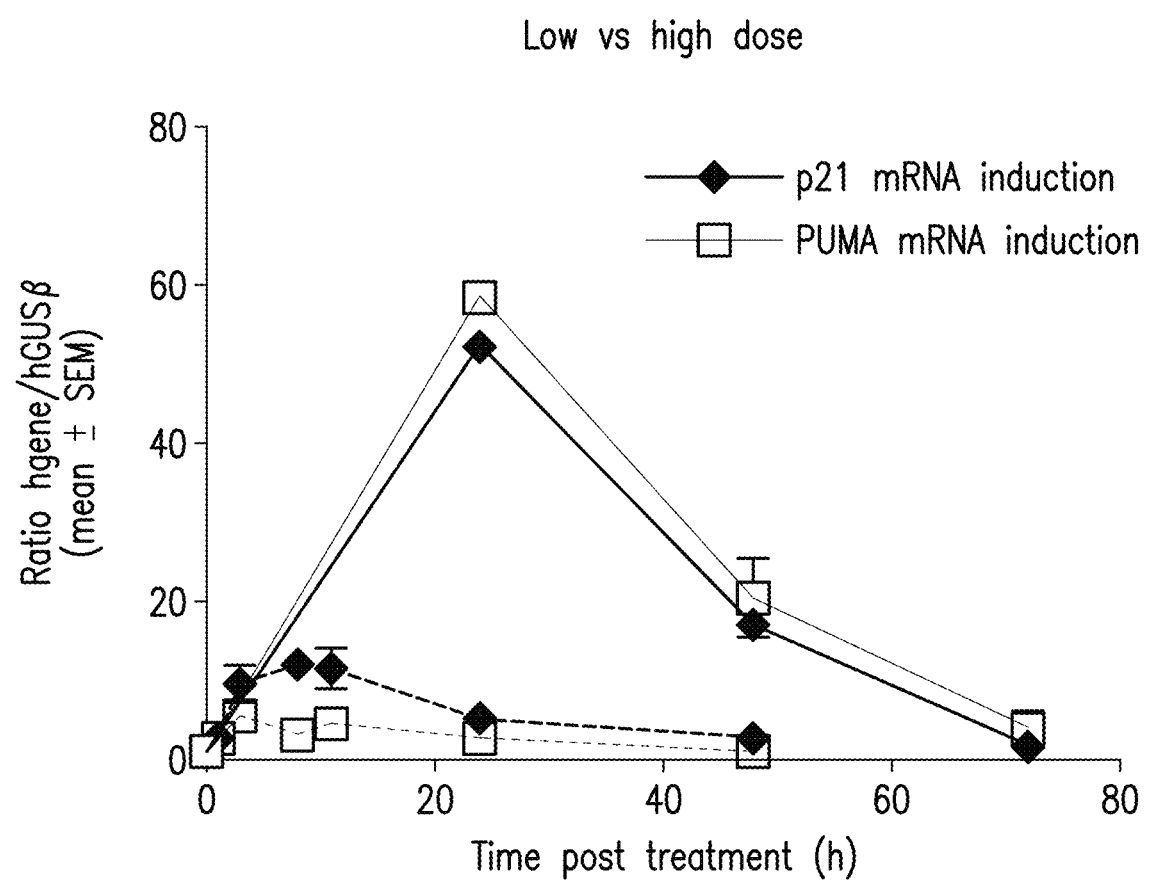
FIG. 16 depicts that the Low dose of Mdm2i does not trigger the same biochemical effect as does a high dose

Experiments were done to evaluate the response of a high dose and a low dose. Animals were treated with low dose of 5 mg/kg p.o. or a high dose of 27 mg/kg p.o. or 20 mg/kg i.v. Low dose of Mdm2i does not trigger the same biochemical effect as does the high dose (FIG. 16).

Example 8

Combination of High and Low Dose Treatment is Highly Synergistic

Figure 17:
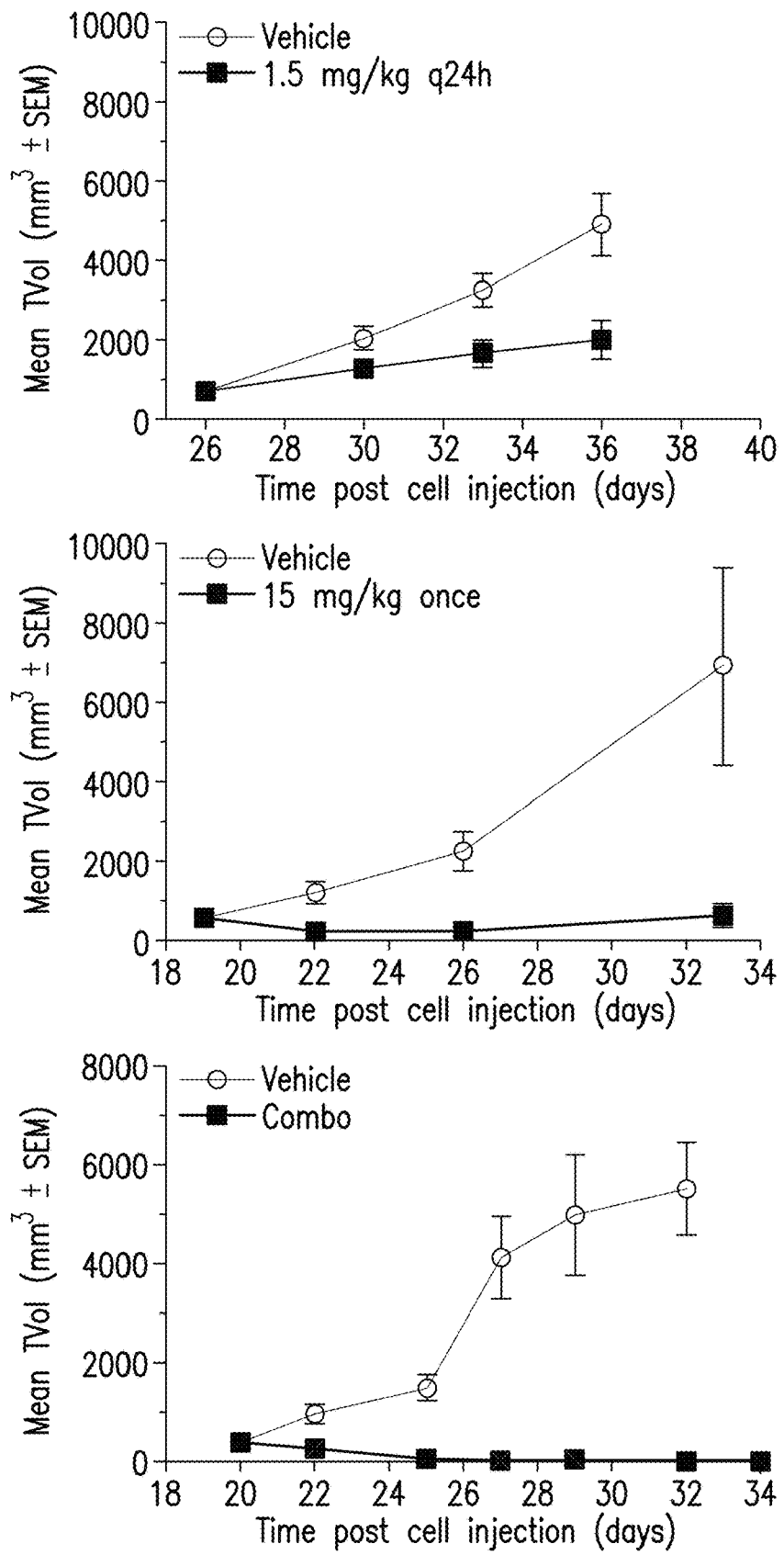
FIG. 17 depicts the Combination of an intermittent and more frequent dosing regimen of Mdm2i having synergistic effect on efficacy
Figure 18:
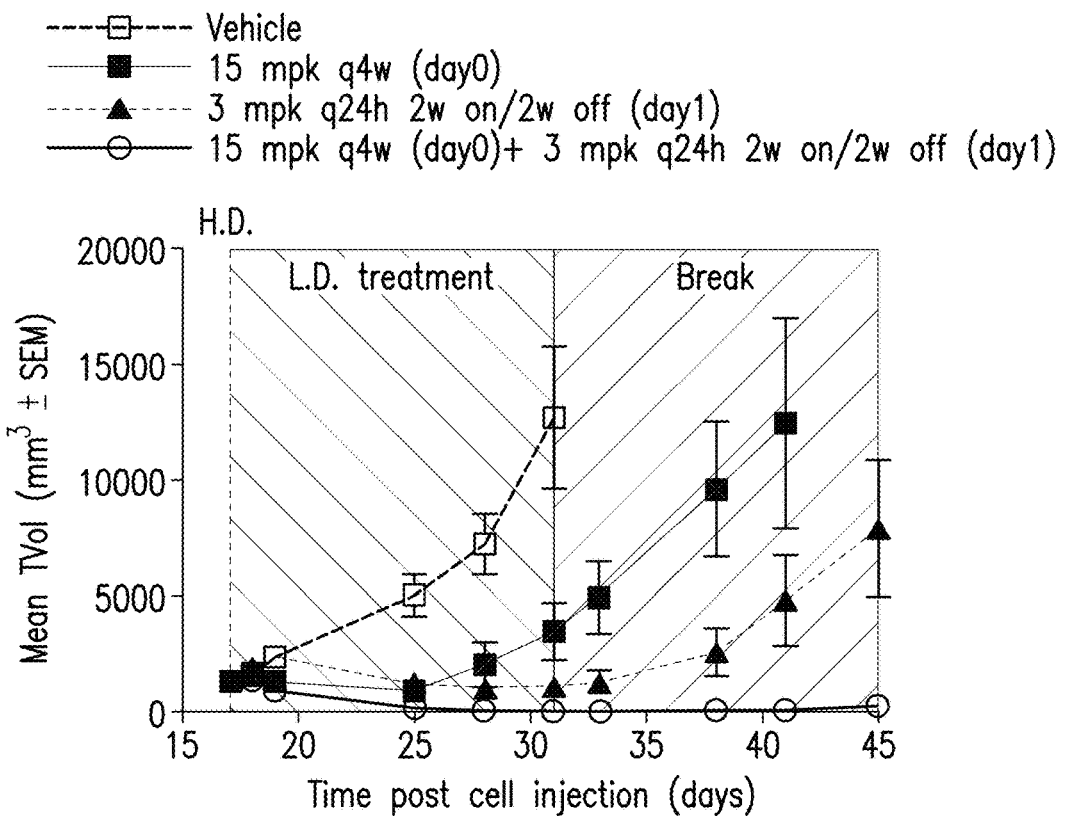
FIG. 18 depicts the Efficacy on SJSA-1 tumor bearing rat after administering Compound A intermittently with a high dose, daily with a low dose and combination of the both dosing schedules
Figure 18:
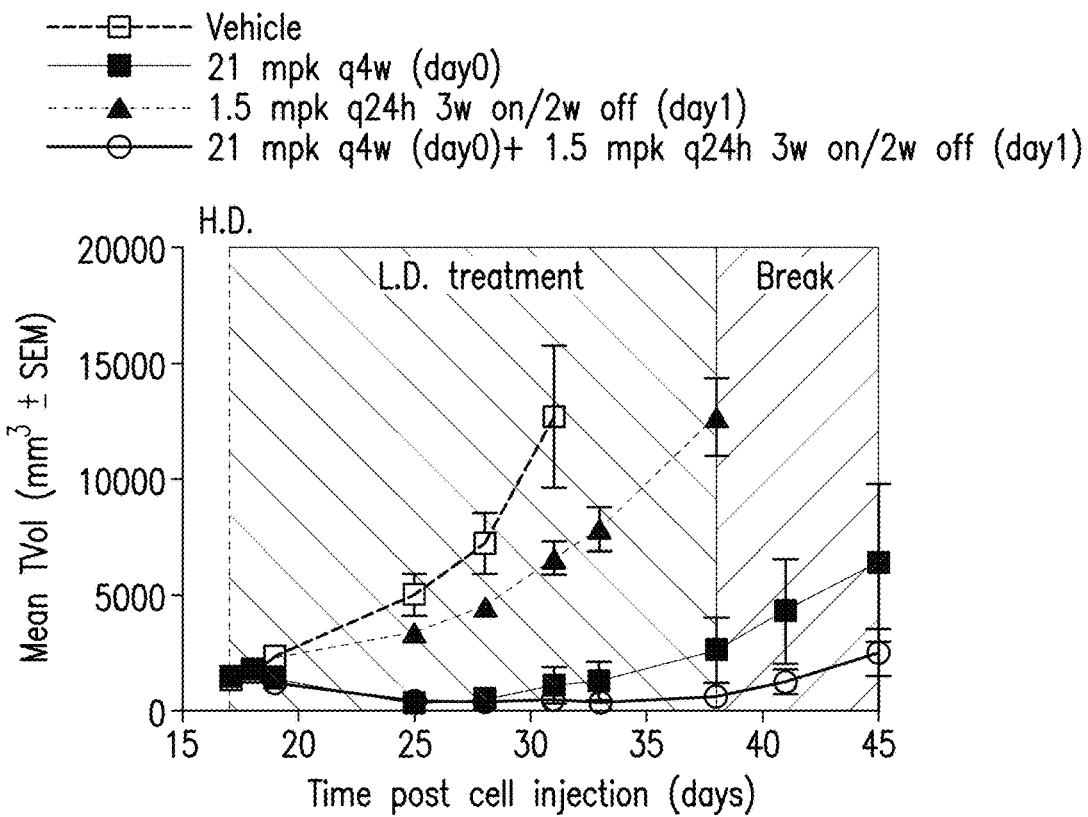
Figure 19:
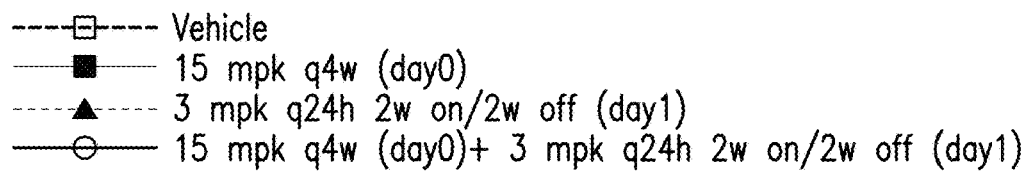
FIG. 19 depicts the Tolerability on SJSA-1 tumor bearing rat after administering Compound A intermittently with a high dose, daily with a low dose and combination of the both dosing schedules
Figure 19:
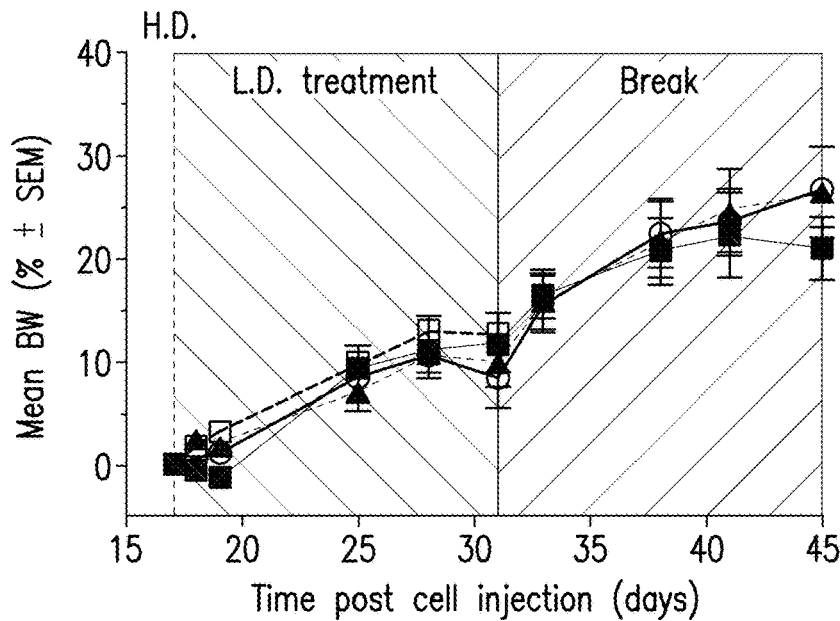
Figure 19:
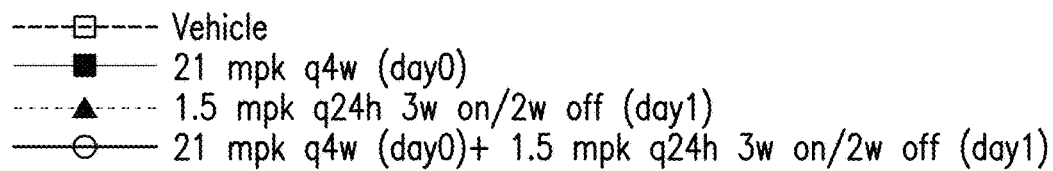
Figure 19:
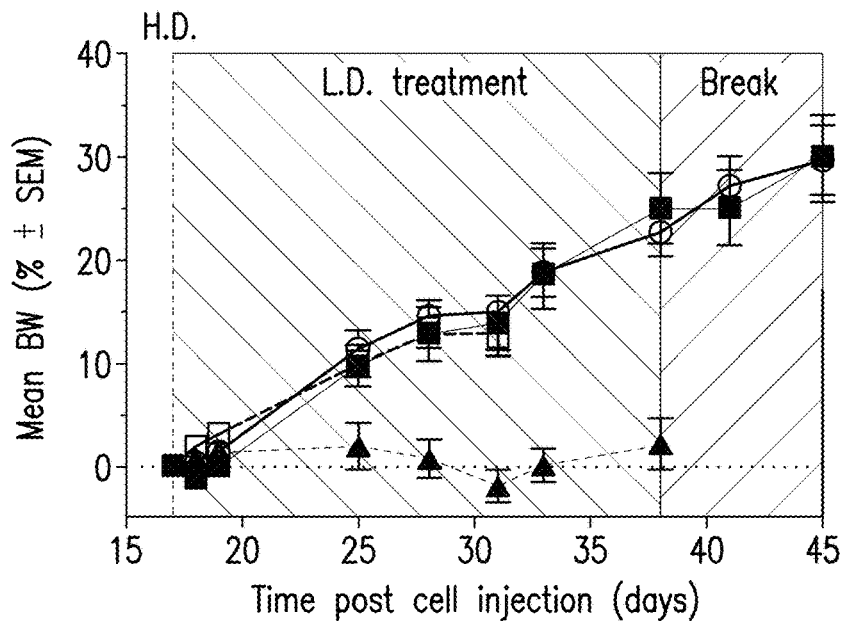

The experiments were repeated on SJSA-1 tumour bearing rats with combining two dosing schedules of compound A, one intermittent (15 mg/kg once) and the daily dosing (1.5 mg/kg). We show on FIG. 17 that combining the two dosing regimens has a highly synergistic effect. This is a schematic presentation of multiple experiments. Further clear synergism can be seen also on FIGS. 18 and 19. Efficacy (FIG. 18) on SJSA-1 tumour bearing rat and tolerability (FIG. 19) was further tested with other doses and different dosing schedules (15 mg/kg q4w (day 0)+3 mg/kg q24 h 2w on/2w off (day 1); 21 mg/kg q4w (day 0)+1.5 mg/kg q24 h 3w on/1w off (day 1). Combining the dosing schedules was shown to improve efficacy and may increase tolerability, particularly as lower doses can be used to still achieve better tumour shrinkage.

Example 9

Efficacy and Tolerability in Melanoma Patient Derived Xenograft (PDX) Bearing Rat (Per Os)

Figure 20:
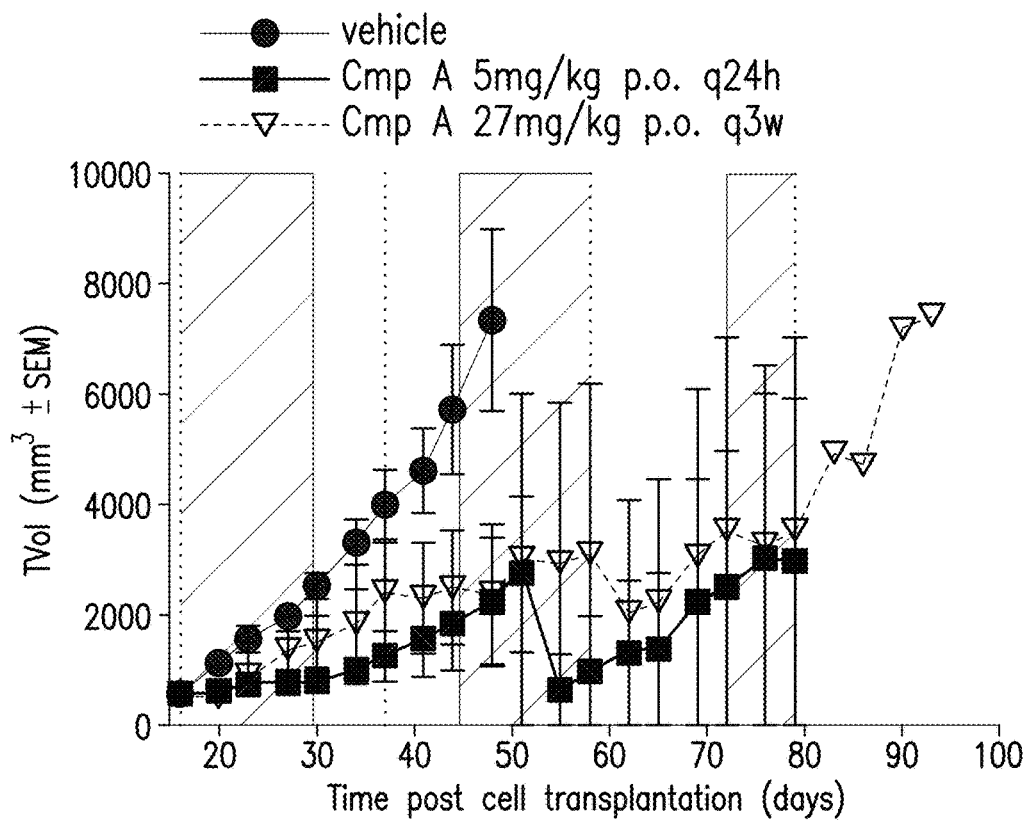
FIG. 20 depicts the Efficacy of Mdm2i at 27 mg/kg q3w per os in melanoma PTX bearing rat. "Cmp A" is an abbreviation for a "Compound A".
Figure 21:
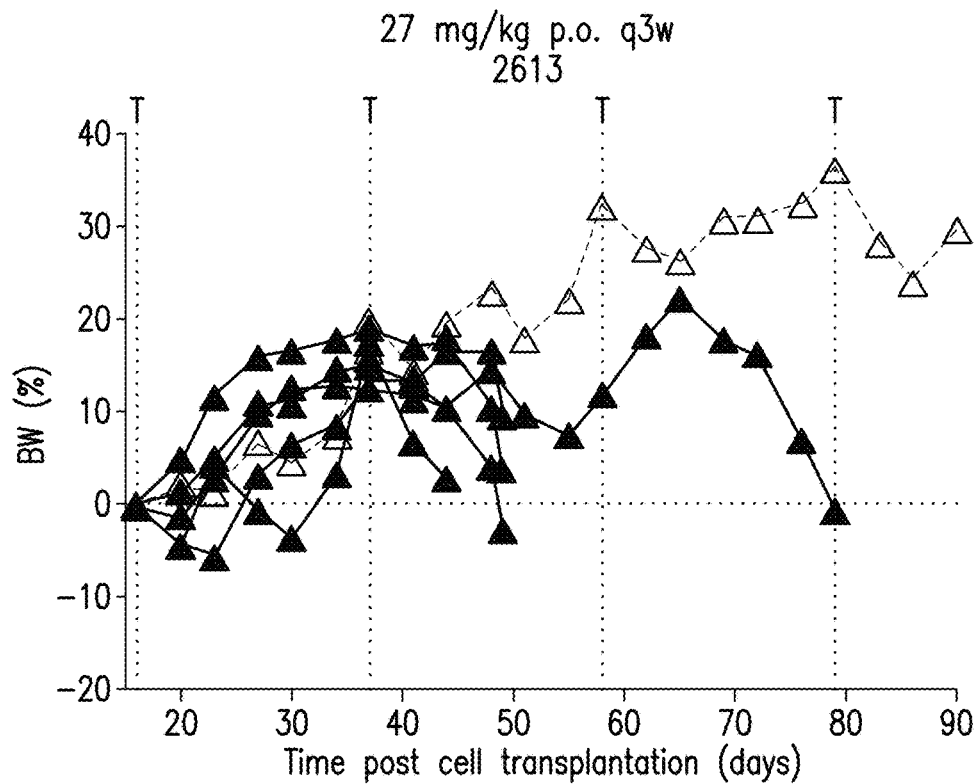
FIG. 21 depicts the Tolerability of Mdm2i at 27 mg/kg q3w per os in melanoma PTX bearing rat

The same experiments were repeated with melanoma PTX bearing rat. Efficacy (FIG. 20) and tolerability (FIG. 21) of compound A was tested at 27 mg/kg q3w. The intermittent dosing showed efficacy also in melanoma models.

Example 10

Figure 22:
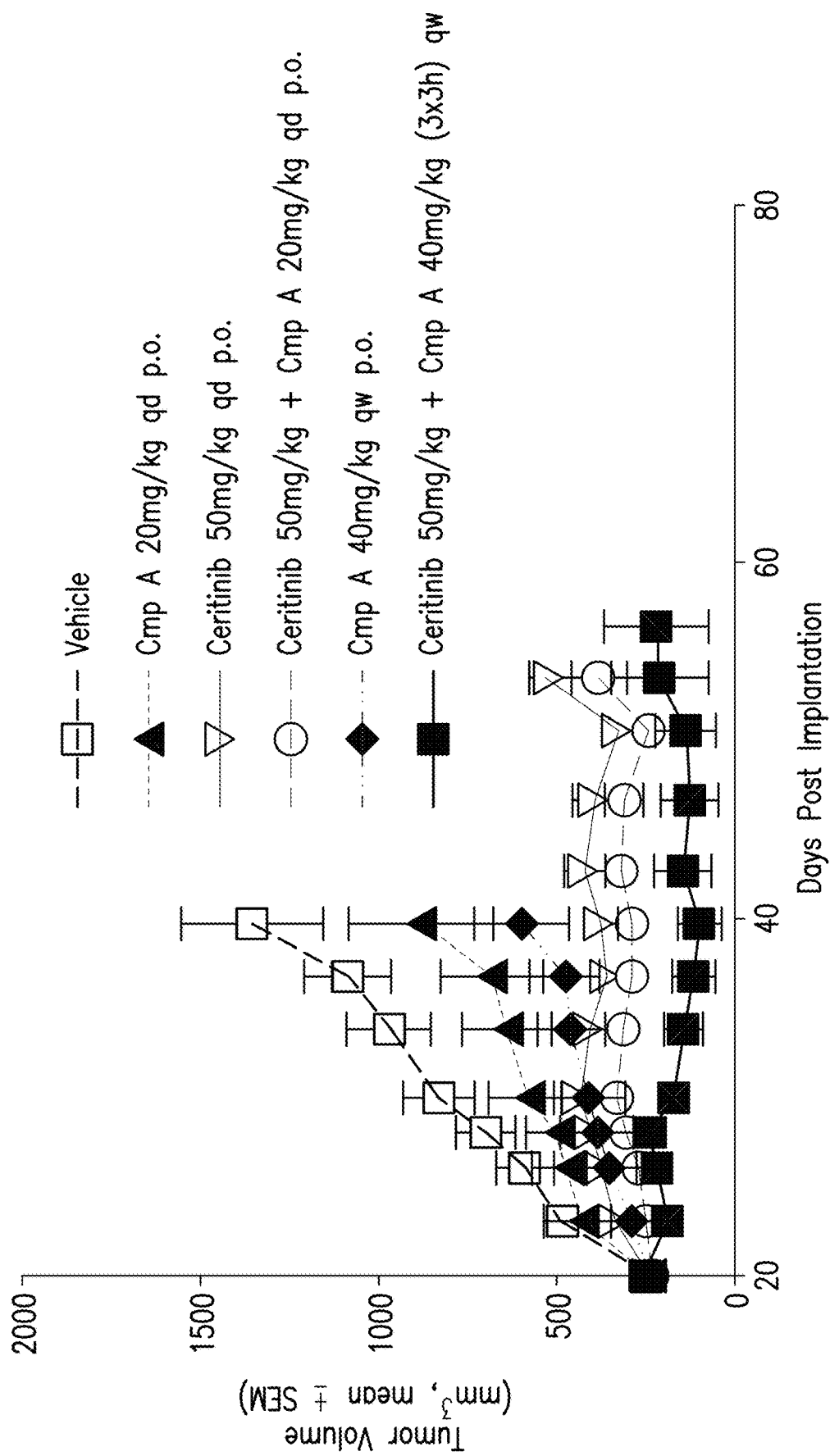
FIG. 22 depicts the Efficacy of intermittently administered compound A in combination with ceritinib in SHSY5Y tumor bearing mice. "Cmp A" is an abbreviation for a "Compound A"

Efficacy of Intermittently Administered Compound a in Combination with Ceritinib in SHSY5Y Tumor Bearing Mice Similar experiments were conducted with administering a combination of Ceritinib and compound A to mice. The experiments showed (FIG. 22) that Compound A can be dosed every week when combined with another compound. Ceritinib with Compound A weekly at 120 mg/kg (40 mg/kg×3 every 3 hours) resulted in better anti-tumor effect compared to ceritinib alone or compared to combination of ceritinib+Compound A daily at 20 mg/kg (n=5). Mice have different pharmacokinetic than rats. Therefore, the dose had to be administered 3 times every 3 hours to achieve the required exposures. Taking this specificity of the mice model into account, particularly a much higher clearance, the experiments on mice can be extrapolated to rats and other subjects and it is believed that the mice model proves that at least the same effect could be achieved in rats or other subjects, particularly human, even if compound A were to be administered at least every three weeks.

The invention claimed is:

1. A method for treating MDM2 related cancers with a MDM2i, wherein said MDM2i is (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, said MDM2i is:
   a) administered orally in an amount of between 100 and 800 mg once every 3 weeks (q3w) in at least three consecutive doses; and
   b) proliferation of said cancer is reduced.

2. The method according to claim 1, wherein said cancer is bladder, breast, brain, head and neck, liver, oral, biliary tract, acute or chronic lymphoid leukemia, acute or chronic myeloid leukemia, chronic myelomonocytic leukemia, colorectal, gastric, gastrointestinal stromal, hepatocellular, glioma, lymphoma, melanoma, multiple myeloma, myeloproliferative disease, neuroendocrine, neuroblastoma, lung, non-small cell lung, pancreatic, ovarian, prostate, renal cell, sarcoma, liposarcoma, or thyroid cancer.

3. The method according to claim 2, wherein the cancer is melanoma, lung cancer, non-small cell lung cancer, acute or chronic lymphoid leukemia, acute or chronic myeloid leukemia, or neuroblastoma.

4. The method according to claim 3, wherein the cancer is melanoma or neuroblastoma.

* * * * *